US008168579B2

(12) United States Patent
Fernandez Prieto et al.

(10) Patent No.: US 8,168,579 B2
(45) Date of Patent: *May 1, 2012

(54) FLUID DETERGENT COMPOSITIONS COMPRISING A DI-AMIDO GELLANT, AND PROCESSES FOR MAKING

(75) Inventors: Susana Fernandez Prieto, Benicarlo-Castellon (ES); Johan Smets, Lubbeek (BE); Beatriu Escuder Gil, Sant Mateu-Castello (ES); Juan Felipe Miravet Celades, Castellon (ES); Vincent Josep Nebot Carda, Vila real-Castellon (ES)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/045,577

(22) Filed: Mar. 11, 2011

(65) Prior Publication Data
US 2011/0220536 A1 Sep. 15, 2011

(30) Foreign Application Priority Data

Mar. 12, 2010 (EP) .................................. 10156371

(51) Int. Cl.
*C11D 1/00* (2006.01)
*C11D 3/26* (2006.01)
*C11D 3/32* (2006.01)

(52) U.S. Cl. ........ 510/303; 510/305; 510/309; 510/321; 510/336; 510/340; 510/356; 510/357; 510/421; 510/422; 510/426; 510/427; 510/501; 564/152; 564/153

(58) Field of Classification Search .................. 510/303, 510/305, 309, 321, 336, 340, 356, 357, 421, 510/422, 426, 427, 501; 564/152, 153
See application file for complete search history.

(56) References Cited

U.S. PATENT DOCUMENTS

| 5,707,952 | A | 1/1998 | Lambremont et al. |
| 7,018,642 | B2 | 3/2006 | Degenhardt et al. |
| 7,534,915 | B2 | 5/2009 | van Bommel et al. |
| 7,708,982 | B2 | 5/2010 | O'Leary et al. |
| 7,910,526 | B2 | 3/2011 | Kakizaki et al. |
| 2004/0247664 | A1 | 12/2004 | Dreja et al. |
| 2006/0089416 | A1 | 4/2006 | Carr |
| 2008/0057005 | A1 | 3/2008 | Lehn et al. |
| 2008/0096780 | A1 | 4/2008 | Veugelers et al. |

FOREIGN PATENT DOCUMENTS

| GB | 1352536 | 5/1974 |
| WO | WO02/094974 | * 11/2002 |

OTHER PUBLICATIONS

Becerril, J.;Bolte, M.; Burguete,M.I.; Galindo, F.; Garcia-Espana, E.; Luis, S. V.; Miravet J. F.J AM. Chem. Soc. 2003, 125, 6677-6686, (May 2003).
International Search Report dated Jul. 14, 2010 containing 6 pages.
Estroff, Lara; Hamilton, Andrew;Chemical Reviews, vol. 104, No. 3, Jan. 1, 2004, 1201-1218.
Sukuzi, M. Tetrahedron Letters, Elsevier, Amsterdam 45 (2004) 5399-5402.
Barnes, D.J.; Chapman, R.L.; Vagg, R.S.; Watton, E.C. , J. Chem. Eng. Data 1978, 23(4), 349-350, (Oct. 1978).
Moll, Maria . Acta Pol. Pharm: 1968, 25(4), 367-373 (Pol), (May 1968).
International Search Report dated Mar. 3, 2011 containing 7 pages.
International Search Report dated Mar. 11, 2011 containing 8 pages for U.S. Appl. No. 13/045,659.

* cited by examiner

*Primary Examiner* — Gregory Delcotto
(74) *Attorney, Agent, or Firm* — Melissa G Krasovec; Leonard W Lewis

(57) ABSTRACT

The invention is directed to a fluid detergent composition comprising a di-amido gellant and a surfactant, and a method for structuring said composition.

11 Claims, 2 Drawing Sheets

FLUID DETERGENT COMPOSITIONS COMPRISING A DI-AMIDO GELLANT, AND PROCESSES FOR MAKING

FIELD OF THE INVENTION

The present invention relates to fluid detergent compositions comprising a structurant that is compatible with a broad range of detergent compositions and does not affect product clarity, and a process for making them.

BACKGROUND OF THE INVENTION

It has long been desired to create a broad range of variants, offering unique benefits, from a single base detergent composition. By adding specific benefit agents to such a base, one could simply and cost-effectively provide compositions that are tailored to a specific group of users. However, a big challenge is to find structurants to thicken such compositions which are compatible with a broad range of potential detergent ingredients.

External structurants for providing rheological benefits to fluid detergent compositions are known. Examples of desired benefits of such structurants include particle suspension, shear thinning properties, a thick appearance on the shelf, as well as stabilization of other materials which are desired to be incorporated within the composition. Known external structurants include those derived from castor oil, fatty acids, fatty esters, or fatty soap water-insoluble waxes. However, their applicability for detergent applications is limited due to degradation by conventional detergent ingredients such as enzymes, including protease and lipase (lipase hydrolyses ester bonds present in castor oil derivatives), which are desirable for improved low temperature cleaning. This class of structurants is also incompatible with low pH and peroxide bleaches. Such external structurants make the detergent compositions less aesthetically pleasing since they impart additional cloudiness and hence reduce the clarity of the composition. For these reasons, formulators have often resorted to polymeric structurants. However, they can result in a stringy pour profile that is undesirable to the consumer, particularly when "gel-like" viscosities are desired.

As such, a need remains for a structurant that is compatible with a broad range of detergent compositions, that does not affect product clarity, while still providing good structuring of the detergent ingredients and being easy to pour.

SUMMARY OF THE INVENTION

The fluid detergent composition of the present invention comprises: from 1% to 70% by weight of a surfactant selected from the group: anionic, nonionic surfactants and mixtures thereof; and from 0.01 wt % to 10 wt % of a di-amido gellant, wherein the diamido gellant comprises at least two amido groups connected via a linking moiety and at least two aminofunctional end-groups. Another aspect of the present invention relates to a method of structuring a liquid detergent composition comprising at least one di-amido gellant.

DETAILED DESCRIPTION OF THE INVENTION

Figure 1:
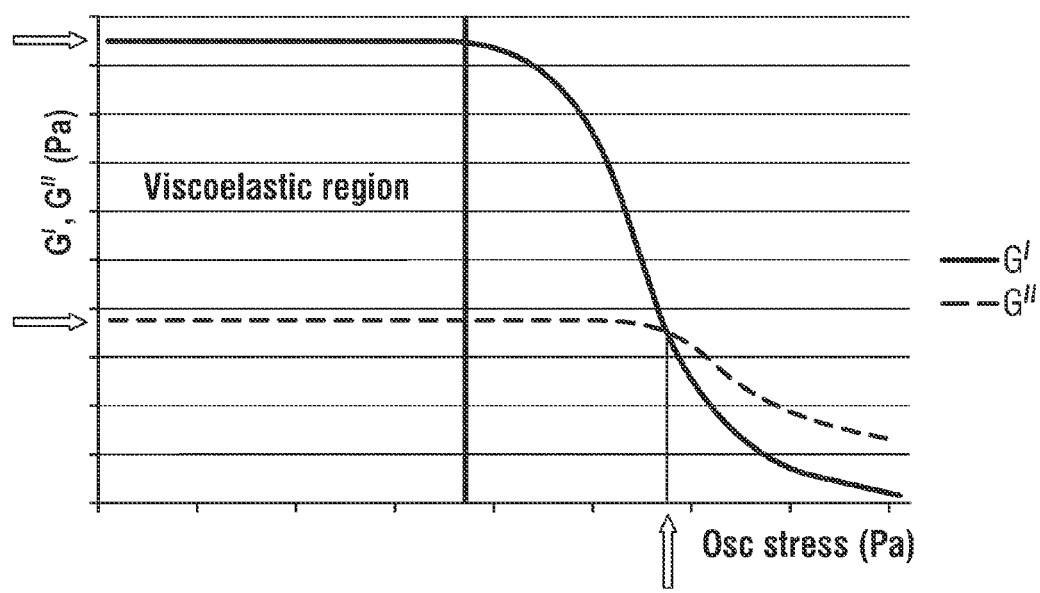
FIG. 1 details G' and G" within the linear viscoelastic region and the oscillation stress at the point where G' and G" cross over as a measure for gel strength.

Fluid detergent compositions as described herein include but are not limited to consumer products such as: shampoos; skin cleaners and exfolients; shaving liquids, foams and gels; products for treating fabrics, hard surfaces and any other surfaces in the area of fabric and home care, including: dishwashing, laundry cleaning, laundry and rinse additives, hard surface cleaning including floor and toilet bowl cleaners; products relating to oral care including toothpastes and gels and whiteners. A particularly preferred embodiment of the invention is a "fluid laundry detergent composition". As used herein, "fluid laundry detergent composition" refers to any laundry treatment composition comprising a fluid capable of wetting and cleaning fabric e.g., clothing, in a domestic washing machine.

The fluid detergent composition can include solids or gases in suitably subdivided form, but the overall composition excludes product forms which are non-fluid overall, such as tablets or granules. The fluid detergent compositions preferably have densities in the range from of 0.9 to 1.3 grams per cubic centimeter, more preferably from 1.00 to 1.10 grams per cubic centimeter, excluding any solid additives but including any bubbles, if present.

The fluid detergent compositions of the invention may be opaque, semi-transparent or even clear. When clarity of the fluid detergent composition is desired, the fluid detergent composition has a turbidity of from 5 NTU to less than 3000 NTU, preferably less than 1000 NTU, more preferably less than 500 NTU and most preferably less than 100 NTU.

All percentages, ratios and proportions used herein are by weight percent of the composition, unless otherwise specified. All average values are calculated "by weight" of the composition or components thereof, unless otherwise expressly indicated.

Anionic and Nonionic Surfactants:

Detergent compositions of the present invention comprise from 1% to 70%, preferably from 5% to 60% by weight, more preferably from 10% to 50%, and most preferably from 15% to 45% by weight of a surfactant selected from the group: anionic, nonionic surfactants and mixtures thereof. The preferred ratio of anionic to nonionic surfactant is from 100:0 (i.e. no nonionic surfactant) to 5:95, more preferably from 99:1 to 1:4, most preferably 5:1 to 1.5:1.

1. Anionic Surfactants:

The fluid detergent compositions of the present invention preferably comprises from 1 to 50%, more preferably from 5 to 40%, most preferably from 10 to 30% by weight of one or more anionic surfactants. Preferred anionic surfactant are selected from the group consisting of: C11-C18 alkyl benzene sulfonates, C10-C20 branched-chain and random alkyl sulfates, C10-C18 alkyl ethoxy sulfates, mid-chain branched alkyl sulfates, mid-chain branched alkyl alkoxy sulfates, C10-C18 alkyl alkoxy carboxylates comprising 1-5 ethoxy units, modified alkylbenzene sulfonate, C12-C20 methyl ester sulfonate, C10-C18 alpha-olefin sulfonate, C6-C20 sulfosuccinates, and mixtures thereof. However, by nature, every anionic surfactant known in the art of detergent compositions may be used, such as disclosed in "Surfactant Science Series", Vol. 7, edited by W. M. Linfield, Marcel Dekker. The compositions of the present invention comprise preferably at least one sulphonic acid surfactant, such as a linear alkyl benzene sulphonic acid, or the water-soluble salt forms.

Anionic sulfonate or sulfonic acid surfactants suitable for use herein include the acid and salt forms of linear or branched C5-C20, more preferably C10-C16, most preferably C11-C13 alkylbenzene sulfonates, C5-C20 alkyl ester sulfonates, C6-C22 primary or secondary alkane sulfonates, C5-C20 sulfonated polycarboxylic acids, and mixtures thereof. The aforementioned surfactants can vary widely in their 2-phenyl isomer content.

Anionic sulphate salts suitable for use in compositions of the invention include: primary and secondary alkyl sulphates, having a linear or branched alkyl or alkenyl moiety having from 9 to 22 carbon atoms, more preferably from 12 to 18 carbon atoms; beta-branched alkyl sulphate surfactants; and mixtures thereof.

Mid-chain branched alkyl sulphates or sulfonates are also suitable anionic surfactants for use in the compositions of the invention. Preferred are the C5-C22, preferably C10-C20 mid-chain branched alkyl primary sulphates. When mixtures are used, a suitable average total number of carbon atoms for the alkyl moieties is preferably within the range of from 14.5 to 17.5. Preferred mono-methyl-branched primary alkyl sulphates are selected from the group consisting of the 3-methyl to 13-methyl pentadecanol sulphates, the corresponding hexadecanol sulphates, and mixtures thereof. Dimethyl derivatives or other biodegradable alkyl sulphates having light branching can similarly be used.

Other suitable anionic surfactants for use herein include fatty methyl ester sulphonates and/or alkyl ethyoxy sulphates (AES) and/or alkyl polyalkoxylated carboxylates (AEC). Mixtures of anionic surfactants can be used, for example mixtures of alkylbenzenesulphonates and AES.

The anionic surfactants are typically present in the form of their salts with alkanolamines or alkali metals such as sodium and potassium. Preferably, the anionic surfactants are neutralized with alkanolamines such as monoethanolamine or triethanolamine, and are fully soluble in the liquid phase.

2. Nonionic Surfactants:

The fluid detergent compositions of the present invention preferably comprise up to 30%, more preferably from 1 to 15%, most preferably from 2 to 10% by weight of one or more nonionic surfactants. Suitable nonionic surfactants include, but are not limited to C12-C18 alkyl ethoxylates ("AE") including the so-called narrow peaked alkyl ethoxylates, C6-C12 alkyl phenol alkoxylates (especially ethoxylates and mixed ethoxy/propoxy), block alkylene oxide condensate of C6-C12 alkyl phenols, alkylene oxide condensates of C8-C22 alkanols and ethylene oxide/propylene oxide block polymers (Pluronic®-BASF Corp.), as well as semi polar nonionics (e.g., amine oxides and phosphine oxides). An extensive disclosure of suitable nonionic surfactants can be found in U.S. Pat. No. 3,929,678.

Alkylpolysaccharides such as disclosed in U.S. Pat. No. 4,565,647 are also useful nonionic surfactants for compositions of the invention. Also suitable are alkyl polyglucoside surfactants. In some embodiments, suitable nonionic surfactants include those of the formula $R_1(OC_2H_4)_nOH$, wherein $R_1$ is a C10-C16 alkyl group or a C8-C12 alkyl phenyl group, and n is from 3 to about 80. In some embodiments, the nonionic surfactants may be condensation products of C12-C15 alcohols with from 5 to 20 moles of ethylene oxide per mole of alcohol, e.g., C12-C13 alcohol condensed with about 6.5 moles of ethylene oxide per mole of alcohol. Additional suitable nonionic surfactants include polyhydroxy fatty acid amides of the formula:

wherein R is a C9-C17 alkyl or alkenyl, $R_1$ is a methyl group and Z is glycidyl derived from a reduced sugar or alkoxylated derivative thereof. Examples are N-methyl N-1-deoxyglucityl cocoamide and N-methyl N-1-deoxyglucityl oleamide.

External Structurant:

The external structurant preferably imparts a shear thinning viscosity profile to the fluid detergent composition, independently from, or extrinsic from, any structuring effect of the detersive surfactants of the composition. Preferred external structurants include those which provide a pouring viscosity from 50 cps to 20,000 cps, more preferably from 200 cps to 10,000 cps, most preferably from 500 cps to 7,000 cps. The fluid detergent composition preferably has a resting viscosity of at least 1,500 cps, preferably at least 10,000 cps, more preferably at least 50,000 cps. This resting (low stress) viscosity represents the viscosity of the fluid detergent composition under gentle shaking in the package and during transportation. Alternatively, the fluid detergent composition may be a thixotropic gel. Such compositions may have a resting viscosity of from 10,000 cps to 500,000 cps, preferably from 100,000 cps to 400,000 cps, more preferably from 200,000 to 300,000. The preferred shear-thinning characteristics of the fluid detergent is defined as a ratio of low stress viscosity to pouring viscosity of at least 2, preferably at least 10, more preferably at least 100, up to 2000.

The pouring viscosity is measured at a shear rate of 20 sec$^{-1}$, which is a shear rate that the fluid detergent composition is typically exposed to during pouring. The resting (low stress) viscosity is determined under a constant stress of 0.1 Pa during a viscosity creep experiment over a 5 minute interval. Rheology measurements over the 5 minute interval are made after the composition has rested at zero shear rate for at least 10 minutes, between loading the sample in the rheometer and running the test. The data over the last 3 minutes are used to fit a straight line, and from the slope of this line, the low stress viscosity is calculated. The viscosity is measured at 21° C. using a TA AR 2000 (or AR G2) rheometer with a 40 mm stainless steel plate having a gap of 500 microns.

1. Di-amido Gellant

The fluid detergent composition includes a di-amido gellant as an external structurant at a level from 0.01 wt % to 10 wt %, preferably from 0.05 wt % to 5 wt %, more preferably from 0.1 wt % to 2 wt %, most preferably from 0.4 wt % to 1 wt %. In an alternative embodiment, the fluid detergent composition comprises from 0.1 wt % to 0.5 wt % of the di-amido gallant.

The di-amido gellant comprises at least two nitrogen atoms, wherein at least two of said nitrogen atoms form amido functional substitution groups. In one embodiment, the amido groups are different. In a preferred embodiment, the amido functional groups are the same. The di-amido gellant has the following formula:

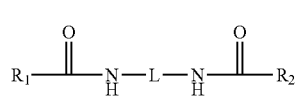

[I]

wherein: $R_1$ and $R_2$ are aminofunctional end-groups which may be the same or different and L is a linking moeity of molecular weight from 14 to 500 g/mol.

In a preferred embodiment: $R_1$ is $R_3$ or $$\underset{H\ or\ R'}{\overset{AA}{\underset{|}{\overset{|}{-}\underset{|}{C}-R_3,}}}$$

and $R_2$ is $R_4$ or $$\underset{H\ or\ R'}{\overset{AA}{\underset{|}{\overset{|}{-}\underset{|}{C}-R_4,}}}$$

wherein AA is selected from the group consisting of:
R'', H, —CH₃, —CH(CH₃)₂ (isopropyl), —CH₂—CH(CH₃)₂ (isobutyl), —CH₂—OH, —CH(OH)CH₃, —CH₂—SH, —CH₂—CH₂—S—CH₃, —CH(CH₃)CH₂CH₃ (sec-butyl), —CH₂—CH₂—CH₂—NH—C(=NH)—NH₂, —CH₂—CH₂—CH₂—CH₂—NH₂, —CH₂—CH₂—C(=O)—NH₂, —CH₂—CH₂—C(=O)—OH, —CH₂—C(=O)—OH, —CH₂-imidazolyl, —CH₂-phenyl, —CH₂-indolyl, —CH₂—C(=O)—NH₂, —CH₂-(4-hydroxyphenyl), and $R_3$ and $R_4$ independently have the formula:

$(L')_m-(L'')_q-R$, where (m+q) is from 1 to 10, [II]

such that $R_1$ and $R_2$ are aminofunctional end-groups.
Preferably, L has the formula:

$A_a-B_b-C_c-D_d$, where (a+b+c+d) is from 1 to 20, [III]

wherein L', L'' from formula [II] and A, B, C, D from formula [III] are independently selected from the group consisting of:

[structures: —C(H or R')(H or R')—, —N(R')—, —C(=O)—, —S(=O)₂—,
—N⁺(H or R')(H or R') X⁻—, —C(=O)—O—, —O—, —N=C(R')—,
—C(=O)—N(R')—, —N=Si(R')(R')—, —O—C(=O)—O—,
—C(=O)—O—O—, —C(H or R')=C(H or R')—,
1,4-phenylene-bis-carbonyl (2,3,5,6 position*), —C≡C—,
cyclobutyl (H or R' substituted), 1,3-phenylene (2,3,5,6 position*),
—O—S(=O)₂—O—, —S(=O)₂—O—, —S(=O)₂—N(R')—,
cyclohexyl (2,3,5,6 position*), cyclopropyl (R' substituted),
cyclopentyl (H or R' substituted), 1,3-phenylene-bis(oxy) disubstituted (with O—H or R')]

Preferably, L', L'' from formula [II] and A, B, C, D from formula [III] are independently selected from the group consisting of:

[structures: —C(H or R')(H or R')—, —N(R')—, —C(=O)—, —S(=O)₂—,
—N⁺(H or R')(H or R') X⁻—, —O—, —N=C(R')—, —C(=O)—N(R')—,
—N=Si(R')(R')—, 1,4-phenylene (2,3,5,6 position*)]

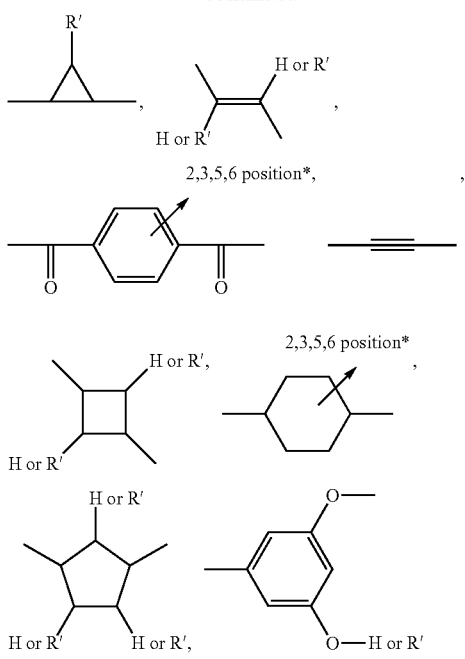
*the arrow indicates up to 4 substitutions in the positions indicated, and $X^-$ an anion and R, R' and R" are independently selected from the group consisting of:
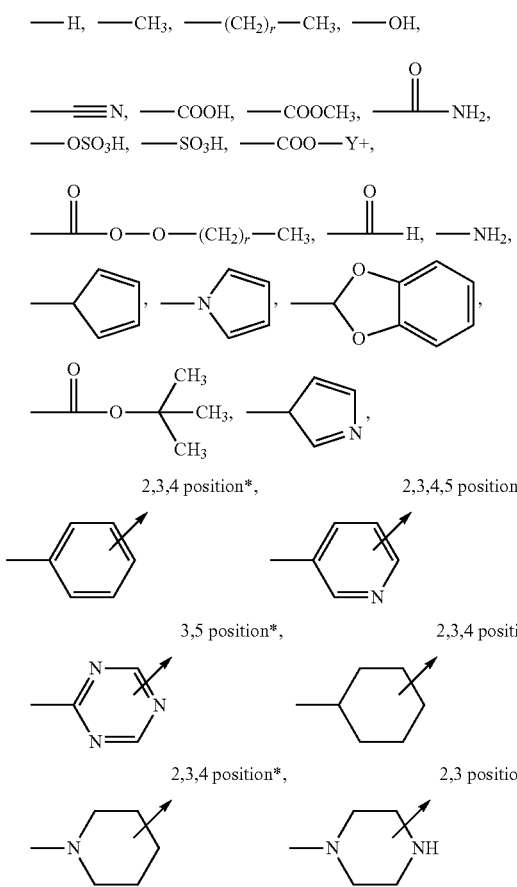
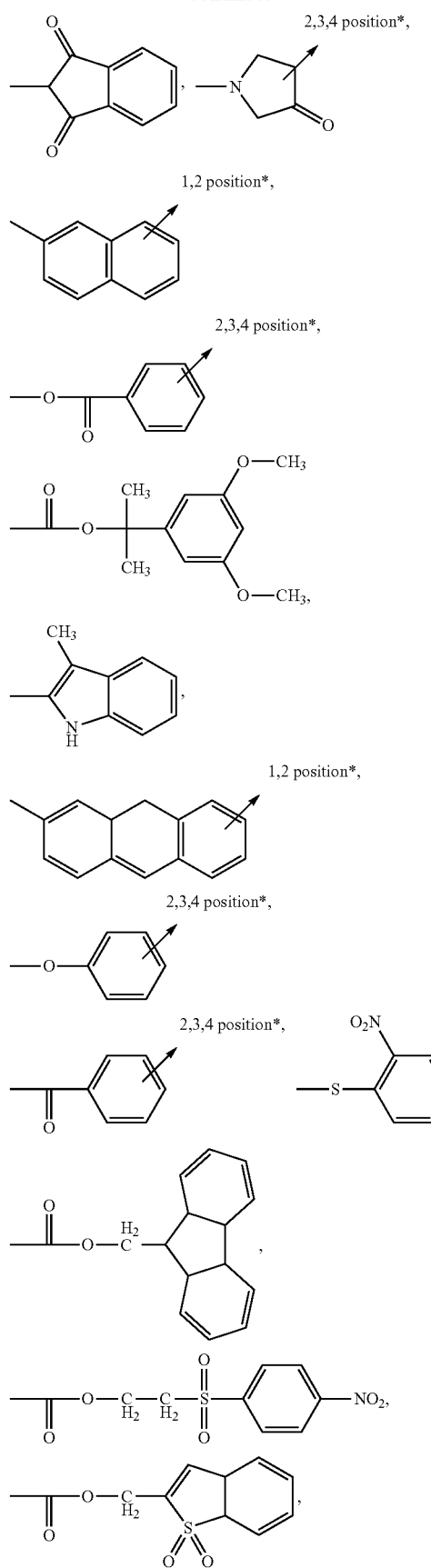

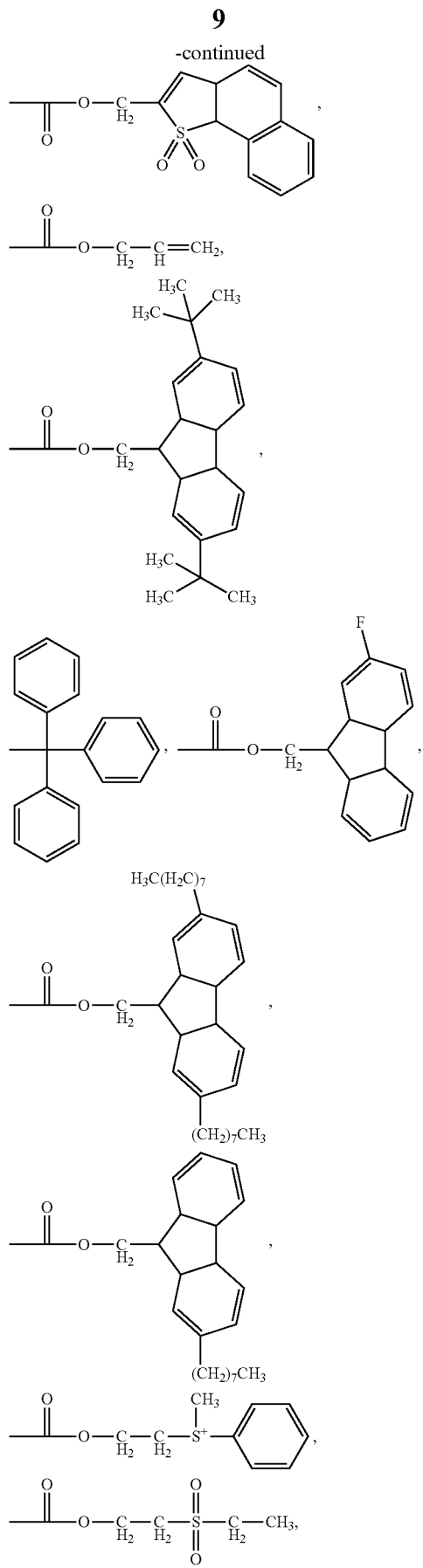
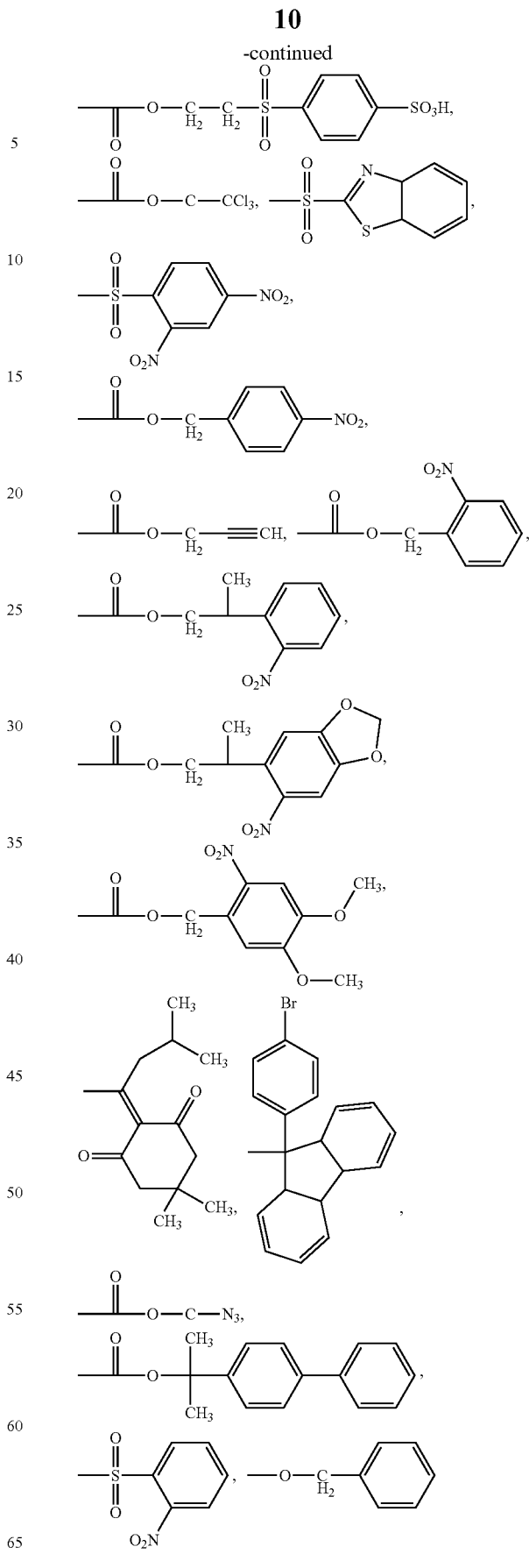

Preferably, R, R' and R" are independently selected from the group consisting of:

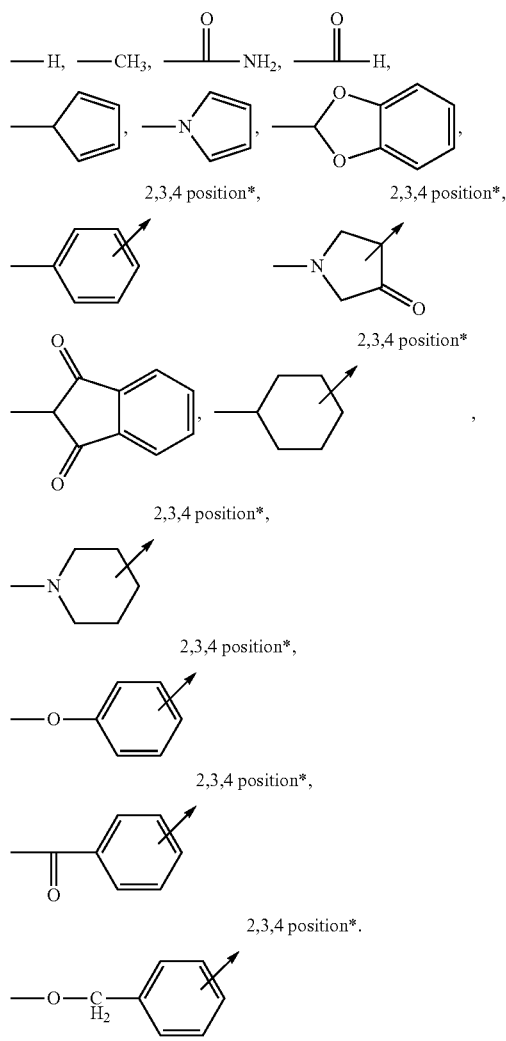

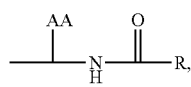

*the arrow indicates up to 4 substitutions in the positions indicated, r is an integer from 1 to 20 and $Y^+$ is a cation.

In a more preferred embodiment, the di-amido gellant is characterized in that:

L is an aliphatic linking group with a backbone chain of from 2 to 20 carbon atoms, preferably —$(CH_2)_n$— wherein n is selected from 2 to 20, and $R_1$ and $R_2$ both have the structure:

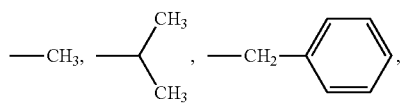

wherein: AA is selected from the group consisting of:

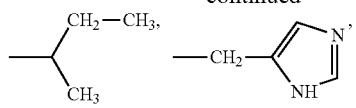

or from the group consisting of:

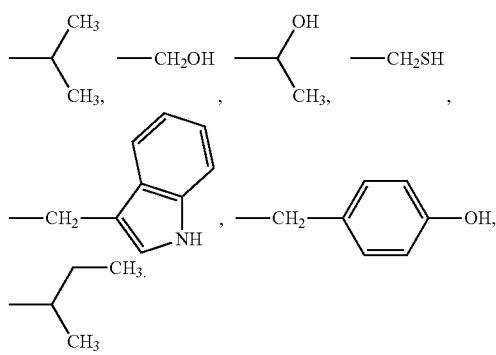

and R is selected from the group:

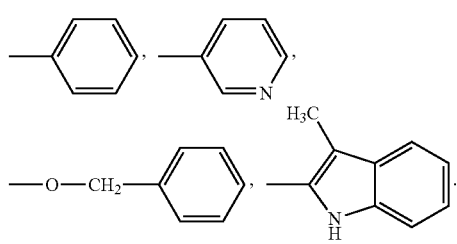

or from the group:

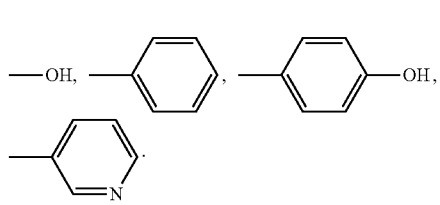

In another embodiment R, R' and R" can independently be selected from the group consisting of: an ethoxy group, an epoxy group with 1 to 15 ethoxy or epoxy units. In another embodiment, the R, R' and R" may comprise a functional end group selected from the group consisting of: an aromatic, alicyclic, heteroaromatic, heterocyclic group including mono-, di-, and oligo-polysaccharides.

Preferably, L is selected from C2 to C20 hydrocarbyl chains, preferably C6 to C12, more preferably C8 to C10. Preferably, the di-amido gellant has a molecular weight from 150 to 1500 g/mol, more preferably from 300 g/mol to 900 g/mol, most preferably from 400 g/mol to 700 g/mol.

In another embodiment, two or more of L, L' and L" are the same group. The di-amido gellant molecule can be symmetric with respect to the L entity or can be asymmetric. Without intending to be bound by theory, it is believed that symmetric di-amido gellant molecules allow for more orderly structured networks to form whereas compositions comprising one or more asymmetric di-amido gellant molecules can create disordered networks. The types of interactions between the di-amido gellant molecules are described in detail hereinafter.

In one embodiment, the AA comprises at least one of: Alanine, β-Alanine and substituted Alanines; Linear Amino-Alkyl Carboxylic Acid; Cyclic Amino-Alkyl Carboxylic Acid; Aminobenzoic Acid Derivatives; Aminobutyric Acid Derivatives; Arginine and Homologues; Asparagine; Aspartic Acid; p-Benzoyl-Phenylalanine; Biphenylalanine; Citrulline; Cyclopropylalanine; Cyclopentylalanine; Cyclohexylalanine; Cysteine, Cystine and Derivatives; Diaminobutyric Acid Derivatives; Diaminopropionic Acid; Glutamic Acid Derivatives; Glutamine; Glycine; Substituted Glycines; Histidine; Homoserine; Indole Derivatives; Isoleucine; Leucine and Derivatives; Lysine; Methionine; Naphthylalanine; Norleucine; Norvaline; Ornithine; Phenylalanine; Ring-Substituted Phenylalanines; Phenylglycine; Pipecolic Acid, Nipecotic Acid and Isonipecotic Acid; Proline; Hydroxyproline; Thiazolidine; Pyridylalanine; Serine; Statine and Analogues; Threonine; Tetrahydronorharman-3-carboxylic Acid; 1,2,3,4-Tetrahydroisoquinoline; Tryptophane; Tyrosine; Valine; and combinations thereof.

The molecule may also comprise protective groups, preferably from 1 to 2 protective groups, preferably two protective groups. Examples of suitable protective groups are provided in "Protecting Groups", P. J. Kocienski, ISBN 313 135601 4, Georg Thieme Verlag, Stuttgart; and "Protective Groups in Organic Chemistry", T. W. Greene, P. G. M. Wuts, ISBN 0-471-62301-6, John Wiley & Sons, Inc, New York. A non-limiting example of a suitable protective group is 9-fluorenylmethoxycarbonyl. N-Benzyloxycarbonyl, N-t-Butyloxycarbonyl.

In one embodiment, the di-amido gellant is a thermoreversible gellant such as described in U.S. Pat. No. 7,332,529. An example of this molecule is provided below:

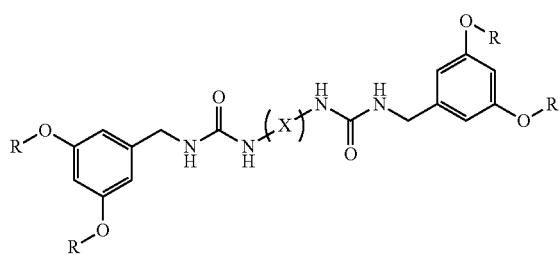

wherein X is C6 to C12 alylene, each R is C9 to C12 alkyl, provided that when X is C6 alkylene, each R must be C10 alkyl. In a preferred embodiment, each R is C10 alkyl. In a more preferred embodiment, each R is C10 alkyl and X is C6 or C12 alkylene. In another embodiment, each R is C12 alkyl. In another preferred embodiment, each R is C12 alkyl and X is C12 alkylene.

The di-amido gellant preferably has a minimum gelling concentration (MGC) of from 0.1 to 100 mg/mL in the fluid detergent composition, preferably from 0.1 to 25 mg/mL, more preferred from 0.5 to 10mg/mL in accordance with the MGC Test Method. The MGC as used herein can be represented as mg/ml or as a wt %, where wt % is calculated as the MGC in mg/ml divided by 10. In one embodiment, when measured in the fluid detergent composition, the MGC is from 0.1 to 100 mg/mL, preferably from 0.1 to 25 mg/mL of said di-amido gellant, more preferably from 0.5 to 10 mg/mL, or at least 0.1 mg/mL, at least 0.3 mg/mL, at least 0.5 mg/mL, at least 1.0 mg/mL, at least 2.0 mg/mL, at least 5.0 mg/mL of di-amido gellant. While the invention includes fluid detergent compositions having a di-amido gellant concentration either above or below the MGC, the di-amido gellants of the invention result in particularly useful rheologies below the MGC.

Suitable di-amido gellants may be selected from table 2, table 3, and mixtures thereof. More preferably, the di-amido gellants are selected from table 3, and mixtures thereof.

To provide more robust structuring, the fluid detergent may comprise a mixture of two or more di-amido gellant structurants. Such a mixture may include a di-amido gellant structurant which has higher solubility in water and/or non-aminofunctional solvents, with a di-amido gellant with lower solubility in water and/or non-aminofunctional solvents. Without intending to be bound by theory, it is believed that a di-amido gellant that is more soluble in water may have difficulty forming a gel in a cleaning composition at a low level, while one that is less soluble, may have difficulty forming a gel because it will be difficult to solubilize it. Mixtures of these two di-amido gellants at different levels show synergies in the way that the one that is more soluble helps to solubilize the other, allowing both to help structure the composition. For instance, dibenzyl(2S,2'S)-1,1'-(propane-1,3-diylbis(azanediyl))bis(3-methyl-1-oxobutane-2,1-diy)dicarbamate has improved solubility when incorporated in combination with the more water-soluble N,N'-(2S,2'S)-1,1'-(propane-1,3-diylbis(azanediyl))bis(3-methyl-1-oxobutane-2,1-diyl)diisonicotinamide.

Di-amido gellant examples of use in the present invention:

TABLE 1

Non-limiting examples of di-amido gellants of use in fluid detergent compositions of the invention:

| Amido Bolaform Example | L | $R_1 = R_2$ |
|---|---|---|
| N,N'-(2S,2'S)-1,1'-(hexane-1,6-diylbis(azanediyl))bis(1-oxopropane-2,1-diyl)diisonicotinamide | —(CH$_2$)$_6$— | |
| 1,1'-(propane-1,3-diyl)bis(3-phenylurea) | —(CH$_2$)$_3$— | |
| N-N'-(2S,2'S)-1,1'-(dodecane-1,12-diylbis(azanediyl))bis(3-(1H-imidazol-5-yl)-1-oxopropane-2,1-diyl)dibenzamide | —(CH$_2$)$_{12}$— | |

TABLE 2

Non-limiting examples of di-amido gellants of use in fluid detergent compositions of the invention:

dibenzyl (2S,2'S)-1,1'-(ethane-1,2-diylbis(azanediyl))bis(3-methyl-1-oxobutane-2,1-diyl)dicarbamate

TABLE 2-continued

Non-limiting examples of di-amido gellants of use in fluid detergent compositions of the invention:

dibenzyl (2S,2'S)-1,1'-(propane-1,3-diylbis(azanediyl))bis(3-methyl-1-oxobutane-2,1-diyl)dicarbamate
dibenzyl (2S,2'S)-1,1'-(butane-1,4-diylbis(azanediyl))bis(3-methyl-1-oxobutane-2,1-diyl)dicarbamate
dibenzyl (2S,2'S)-1,1'-(pentane-1,5-diylbis(azanediyl))bis(3-methyl-1-oxobutane-2,1-diyl)dicarbamate
dibenzyl (2S,2'S)-1,1'-(hexane-1,6-diylbis(azanediyl))bis(3-methyl-1-oxobutane-2,1-diyl)dicarbamate
dibenzyl (2S,2'S)-1,1'-(heptane-1,7-diylbis(azanediyl))bis(3-methyl-1-oxobutane-2,1-diyl)dicarbamate
dibenzyl (2S,2'S)-1,1'-(octane-1,8-diylbis(azanediyl))bis(3-methyl-1-oxobutane-2,1-diyl)dicarbamate
dibenzyl (2S,2'S)-1,1'-(nonane-1,9-diylbis(azanediyl))bis(3-methyl-1-oxobutane-2,1-diyl)dicarbamate
dibenzyl (2S,2'S)-1,1'-(decane-1,10-diylbis(azanediyl))bis(3-methyl-1-oxobutane-2,1-diyl)dicarbamate
dibenzyl (2S,2'S)-1,1'-(undecane-1,11-diylbis(azanediyl))bis(3-methyl-1-oxobutane-2,1-diyl)dicarbamate
dibenzyl (2S,2'S)-1,1'-(dodecane-1,12-diylbis(azanediyl))bis(3-methyl-1-oxobutane-2,1-diyl)dicarbamate
dibenzyl (2S,2'S)-1,1'-(tridecane-1,13-diylbis(azanediyl))bis(3-methyl-1-oxobutane-2,1-diyl)dicarbamate
dibenzyl (2S,2'S)-1,1'-(hexadecane-1,16-diylbis(azanediyl))bis(3-methyl-1-oxobutane-2,1-diyl)dicarbamate
dibenzyl (2S,2'S)-1,1'-(octodecane-1,18-diylbis(azanediyl))bis(3-methyl-1-oxobutane-2,1-diyl)dicarbamate
dibenzyl (2S,2'S)-1,1'-(tetradecane-1,14-diylbis(azanediyl))bis(3-methyl-1-oxobutane-2,1-diyl)dicarbamate

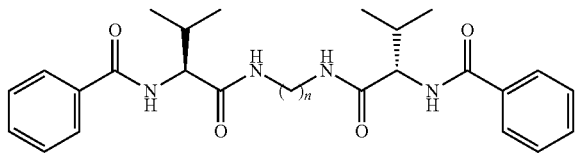

N,N'-(2S,2'S)-1,1'-(ethane-1,2-diylbis(azanediyl))bis(3-methyl-1-oxobutane-2,1-diyl)dibenzamide
N,N'-(2S,2'S)-1,1'-(butane-1,4-diylbis(azanediyl))bis(3-methyl-1-oxobutane-2,1-diyl)dibenzamide
N,N'-(2S,2'S)-1,1'-(propane-1,3-diylbis(azanediyl))bis(3-methyl-1-oxobutane-2,1-diyl)dibenzamide
N,N'-(2S,2'S)-1,1'-(hexane-1,6-diylbis(azanediyl))bis(3-methyl-1-oxobutane-2,1-diyl)dibenzamide
N,N'-(2S,2'S)-1,1'-(pentane-1,5-diylbis(azanediyl))bis(3-methyl-1-oxobutane-2,1-diyl)dibenzamide
N,N'-(2S,2'S)-1,1'-(octane-1,8-diylbis(azanediyl))bis(3-methyl-1-oxobutane-2,1-diyl)dibenzamide
N,N'-(2S,2'S)-1,1'-(heptane-1,7-diylbis(azanediyl))bis(3-methyl-1-oxobutane-2,1-diyl)dibenzamide
-(2S,2'S)-1,1'-(decane-1,10-diylbis(azanediyl))bis(3-methyl-1-oxobutane-2,1-diyl)dibenzamide
N,N'-(2S,2'S)-1,1'-(nonane-1,9-diylbis(azanediyl))bis(3-methyl-1-oxobutane-2,1-diyl)dibenzamide
N,N'-(2S,2'S)-1,1'-(dodecane-1,12-diylbis(azanediyl))bis(3-methyl-1-oxobutane-2,1-diyl)dibenzamide
N,N'-(2S,2'S)-1,1'-(undecane-1,11-diylbis(azanediyl))bis(3-methyl-1-oxobutane-2,1-diyl)dibenzamide
N,N'-(2S,2'S)-1,1'-(hexadecane-1,16-diylbis(azanediyl))bis(3-methyl-1-oxobutane-2,1-diyl)dibenzamide
N,N'-(2S,2'S)-1,1'-(tridecane-1,13-diylbis(azanediyl))bis(3-methyl-1-oxobutane-2,1-diyl)dibenzamide
N,N'-(2S,2'S)-1,1'-(tetradecane-1,14-diylbis(azanediyl))bis(3-methyl-1-oxobutane-2,1-diyl)dibenzamide
N,N'-(2S,2'S)-1,1'-(octadecane-1,18-diylbis(azanediyl))bis(3-methyl-1-oxobutane-2,1-diyl)dibenzamide

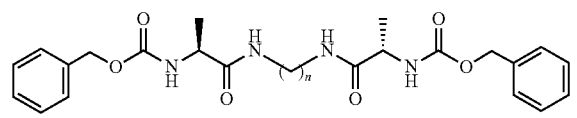

dibenzyl (2S,2'S)-1,1'-(ethane-1,2-diylbis(azanediyl))bis(1-oxopropane-2,1-diyl)dicarbamate
dibenzyl (2S,2'S)-1,1'-(propane-1,3-diylbis(azanediyl))bis(1-oxopropane-2,1-diyl)dicarbamate
dibenzyl (2S,2'S)-1,1'-(butane-1,4-diylbis(azanediyl))bis(1-oxopropane-2,1-diyl)dicarbamate
dibenzyl (2S,2'S)-1,1'-(pentane-1,5-diylbis(azanediyl))bis(1-oxopropane-2,1-diyl)dicarbamate
dibenzyl (2S,2'S)-1,1'-(hexane-1,6-diylbis(azanediyl))bis(1-oxopropane-2,1-diyl)dicarbamate
dibenzyl (2S,2'S)-1,1'-(heptane-1,7-diylbis(azanediyl))bis(1-oxopropane-2,1-diyl)dicarbamate
dibenzyl (2S,2'S)-1,1'-(octane-1,8-diylbis(azanediyl))bis(1-oxopropane-2,1-diyl)dicarbamate
dibenzyl (2S,2'S)-1,1'-(nonane-1,9-diylbis(azanediyl))bis(1-oxopropane-2,1-diyl)dicarbamate
dibenzyl (2S,2'S)-1,1'-(decane-1,10-diylbis(azanediyl))bis(1-oxopropane-2,1-diyl)dicarbamate
dibenzyl (2S,2'S)-1,1'-(undecane-1,11-diylbis(azanediyl))bis(1-oxopropane-2,1-diyl)dicarbamate
dibenzyl (2S,2'S)-1,1'-(dodecane-1,12-diylbis(azanediyl))bis(1-oxopropane-2,1-diyl)dicarbamate
dibenzyl (2S,2'S)-1,1'-(tridecane-1,13-diylbis(azanediyl))bis(1-oxopropane-2,1-diyl)dicarbamate
dibenzyl (2S,2'S)-1,1'-(hexadecane-1,16-diylbis(azanediyl))bis(1-oxopropane-2,1-diyl)dicarbamate
dibenzyl (2S,2'S)-1,1'-(octadecane-1,18-diylbis(azanediyl))bis(1-oxopropane-2,1-diyl)dicarbamate
dibenzyl (2S,2'S)-1,1'-(tetradecane-1,14-diylbis(azanediyl))bis(1-oxopropane-2,1-diyl)dicarbamate

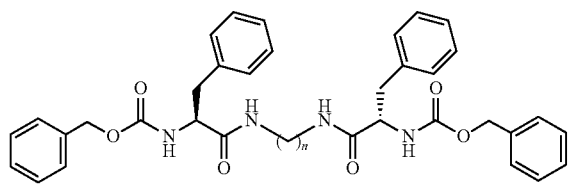

dibenzyl (2S,2'S)-1,1'-(propane-1,3-diylbis(azanediyl))bis(1-oxo-3-phenylpropane-2,1-diyl)dicarbamate
dibenzyl (2S,2'S)-1,1'-(ethane-1,2-diylbis(azanediyl))bis(1-oxo-3-phenylpropane-2,1-diyl)dicarbamate
dibenzyl (2S,2'S)-1,1'-(pentane-1,5-diylbis(azanediyl))bis(1-oxo-3-phenylpropane-2,1-diyl)dicarbamate
dibenzyl (2S,2'S)-1,1'-(butane-1,4-diylbis(azanediyl))bis(1-oxo-3-phenylpropane-2,1-diyl)dicarbamate
dibenzyl (2S,2'S)-1,1'-(heptane-1,7-diylbis(azanediyl))bis(1-oxo-3-phenylpropane-2,1-diyl)dicarbamate
dibenzyl (2S,2'S)-1,1'-(hexane-1,6-diylbis(azanediyl))bis(1-oxo-3-phenylpropane-2,1-diyl)dicarbamate
dibenzyl (2S,2'S)-1,1'-(decane-1,10-diylbis(azanediyl))bis(1-oxo-3-phenylpropane-2,1-diyl)dicarbamate
dibenzyl (2S,2'S)-1,1'-(nonane-1,9-diylbis(azanediyl))bis(1-oxo-3-phenylpropane-2,1-diyl)dicarbamate
dibenzyl (2S,2'S)-1,1'-(dodecane-1,12-diylbis(azanediyl))bis(1-oxo-3-phenylpropane-2,1-diyl)dicarbamate
dibenzyl (2S,2'S)-1,1'-(undecane-1,11-diylbis(azanediyl))bis(1-oxo-3-phenylpropane-2,1-diyl)dicarbamate
dibenzyl (2S,2'S)-1,1'-(hexadecane-1,16-diylbis(azanediyl))bis(1-oxo-3-phenylpropane-2,1-diyl)dicarbamate
dibenzyl (2S,2'S)-1,1'-(tridecane-1,13-diylbis(azanediyl))bis(1-oxo-3-phenylpropane-2,1-diyl)dicarbamate
dibenzyl (2S,2'S)-1,1'-(tetradecane-1,14-diylbis(azanediyl))bis(1-oxo-3-phenylpropane-2,1-diyl)dicarbamate
dibenzyl (2S,2'S)-1,1'-(octadecane-1,18-diylbis(azanediyl))bis(1-oxo-3-phenylpropane-2,1-diyl)dicarbamate

TABLE 2-continued

Non-limiting examples of di-amido gellants of use
in fluid detergent compositions of the invention:

[Chemical structure: dibenzamide with two phenylpropane groups connected by -(CH₂)ₙ- linker]

N-N'-(2S,2'S)-1,1'-(decane-1,10-diylbis(azanediyl))bis(1-oxo-3-phenylpropane-2,1-diyl)dibenzamide
N-N'-(2S,2'S)-1,1'-(nonane-1,9-diylbis(azanediyl))bis(1-oxo-3-phenylpropane-2,1-diyl)dibenzamide
N-N'-(2S,2'S)-1,1'-(dodecane-1,12-diylbis(azanediyl))bis(1-oxo-3-phenylpropane-2,1-diyl)dibenzamide
N-N'-(2S,2'S)-1,1'-(undecane-1,11-diylbis(azanediyl))bis(1-oxo-3-phenylpropane-2,1-diyl)dibenzamide
N-N'-(2S,2'S)-1,1'-(hexadecane-1,16-diylbis(azanediyl))bis(1-oxo-3-phenylpropane-2,1-diyl)dibenzamide
N-N'-(2S,2'S)-1,1'-(tridecane-1,13-diylbis(azanediyl))bis(1-oxo-3-phenylpropane-2,1-diyl)dibenzamide
N-N'-(2S,2'S)-1,1'-(tetradecane-1,14-diylbis(azanediyl))bis(1-oxo-3-phenylpropane-2,1-diyl)dibenzamide
N-N'-(2S,2'S)-1,1'-(octadecane-1,18-diylbis(azanediyl))bis(1-oxo-3-phenylpropane-2,1-diyl)dibenzamide

TABLE 3

Non-limiting examples of preferred di-amido gellants
of use in fluid detergent compositions of the invention:

[Chemical structure: dibenzamide with two phenylpropane groups connected by -(CH₂)ₙ- linker]

N-N'-(2S,2'S)-1,1'-(ethane-1,2-diylbis(azanediyl))bis(1-oxo-3-phenylpropane-2,1-diyl)dibenzamide
N-N'-(2S,2'S)-1,1'-(propane-1,3-diylbis(azanediyl))bis(1-oxo-3-phenylpropane-2,1-diyl)dibenzamide
N-N'-(2S,2'S)-1,1'-(butane-1,4-diylbis(azanediyl))bis(1-oxo-3-phenylpropane-2,1-diyl)dibenzamide
N-N'-(2S,2'S)-1,1'-(pentane-1,5-diylbis(azanediyl))bis(1-oxo-3-phenylpropane-2,1-diyl)dibenzamide
N-N'-(2S,2'S)-1,1'-(hexane-1,6-diylbis(azanediyl))bis(1-oxo-3-phenylpropane-2,1-diyl)dibenzamide
N-N'-(2S,2'S)-1,1'-(heptane-1,7-diylbis(azanediyl))bis(1-oxo-3-phenylpropane-2,1-diyl)dibenzamide
N-N'-(2S,2'S)-1,1'-(octane-1,8-diylbis(azanediyl))bis(1-oxo-3-phenylpropane-2,1-diyl)dibenzamide

[Chemical structure: dibenzamide with two alanine-like groups connected by -(CH₂)ₙ- linker with stereochemistry]

N,N'-(2S,2'S)-1,1'-(propane-1,3-diylbis(azanediyl))bis(1-oxopropane-2,1-diyl)dibenzamide
N,N'-(2S,2'S)-1,1'-(ethane-1,2-diylbis(azanediyl))bis(1-oxopropane-2,1-diyl)dibenzamide
N,N'-(2S,2'S)-1,1'-(pentane-1,5-diylbis(azanediyl))bis(1-oxopropane-2,1-diyl)dibenzamide

TABLE 3-continued

Non-limiting examples of preferred di-amido gellants
of use in fluid detergent compositions of the invention:

N,N'-(2S,2'S)-1,1'-(butane-1,4-diylbis(azanediyl))bis(1-oxopropane-2,1-diyl)dibenzamide
N,N'-(2S,2'S)-1,1'-(heptane-1,7-diylbis(azanediyl))bis(1-oxopropane-2,1-diyl)dibenzamide
N,N'-(2S,2'S)-1,1'-(hexane-1,6-diylbis(azanediyl))bis(1-oxopropane-2,1-diyl)dibenzamide
N,N'-(2S,2'S)-1,1'-(nonane-1,9-diylbis(azanediyl))bis(1-oxopropane-2,1-diyl)dibenzamide
N,N'-(2S,2'S)-1,1'-(octane-1,8-diylbis(azanediyl))bis(1-oxopropane-2,1-diyl)dibenzamide
N,N'-(2S,2'S)-1,1'-(undecane-1,11-diylbis(azanediyl))bis(1-oxopropane-2,1-diyl)dibenzamide
N,N'-(2S,2'S)-1,1'-(decane-1,10-diylbis(azanediyl))bis(1-oxopropane-2,1-diyl)dibenzamide
N,N'-(2S,2'S)-1,1'-(tridecane-1,13-diylbis(azanediyl))bis(1-oxopropane-2,1-diyl)dibenzamide
N,N'-(2S,2'S)-1,1'-(dodecane-1,12-diylbis(azanediyl))bis(1-oxopropane-2,1-diyl)dibenzamide
N,N'-(2S,2'S)-1,1'-(octadecane-1,18-diylbis(azanediyl))bis(1-oxopropane-2,1-diyl)dibenzamide
N,N'-(2S,2'S)-1,1'-(hexadecane-1,16-diylbis(azanediyl))bis(1-oxopropane-2,1-diyl)dibenzamide
dibenzyl (2S-2'S)-1,1'-(octane-1,8-diylbis(azanediyl))bis(1-oxo-3-phenylpropane-2,1-diyl)dicarbamate
N,N'-(2S,2'S)-1,1'-(tetradecane-1,14-diylbis(azanediyl))bis(1-oxopropane-2,1-diyl)dibenzamide 2. Secondary External Structurants In one embodiment, the di-amido gellant is combined with from 0.01 to 5% by weight of one or more additional external structurants. Without being limited by theory, it is believed that the use of an additional external structurant permits improved control of the time-dependent gelling. For example, while the di-amido gellant provides ultimately superior gelling, other external structurants may provide a temporary gel structure while the di-amido gellant is still undergoing gelling. Non-limiting examples of suitable secondary structurants are:

i. Di-benzylidene Polyol Acetal Derivative: The fluid detergent composition may comprise from 0.01% to 1% by weight of a dibenzylidene polyol acetal derivative (DBPA), preferably from 0.05% to 0.8%, more preferably from 0.1% to 0.6%, most preferably from 0.3% to 0.5%. In one embodiment, the DBPA derivative may comprise a dibenzylidene sorbitol acetal derivative (DBS).

ii. Bacterial Cellulose: The fluid detergent composition may also comprise from 0.005% to 1.0% by weight of a bacterial cellulose network. The term "bacterial cellulose" encompasses any type of cellulose produced via fermentation of a bacteria of the genus Acetobacter such as CELLULON® by CPKelco U.S. and includes materials referred to popularly as microfibrillated cellulose, reticulated bacterial cellulose, and the like.

iii. Coated Bacterial Cellulose: In one embodiment, the bacterial cellulose is at least partially coated with a polymeric thickener, for instance, as prepared in accordance with the methods disclosed in US 2007/0027108 paragraphs 8 to 19. In one embodiment the at least partially coated bacterial cellulose comprises from 0.1% to 5%, preferably from 0.5% to 3.0%, by weight of bacterial cellulose; and from 10% to 90% by weight of the polymeric thickener. Suitable bacterial cellulose include the bacterial cellulose described above and suitable polymeric thickeners include: carboxymethylcellulose, cationic hydroxymethylcellulose, and mixtures thereof.

iv. Non-Polymeric Crystalline Hydroxyl-Functional Materials: In a preferred embodiment, the composition further comprises from 0.01 to 1% by weight of the composition of a non-polymeric crystalline, hydroxyl functional structurant. Such non-polymeric crystalline, hydroxyl functional structurants generally comprise a crystallizable glyceride which can be pre-emulsified to aid dispersion into the final fluid detergent composition. Preferred crystallizable glycerides include hydrogenated castor oil or "HCO" or derivatives thereof, provided that it is capable of crystallizing in the liquid detergent composition.

v. Polymeric Structuring Agents: Fluid detergent compositions of the present invention may comprise from 0.01 to 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof. In a preferred embodiment, the polyacrylate is a copolymer of unsaturated mono- or di-carbonic acid and C1-C30 alkyl ester of the (meth)acrylic acid.

Water and/or Non-aminofunctional Organic Solvent:

The fluid detergent composition may be dilute or concentrated aqueous liquids. Alternatively, the fluid detergent composition may be almost entirely non-aqueous, and comprise a non-aminofunctional organic solvent. Such fluid detergent compositions may contain very little water, for instance, that may be introduced with other raw materials. Preferably, the fluid detergent composition comprises from 1% to 95% by weight of water and/or non-aminofunctional organic solvent. For concentrated detergents, the composition comprises preferably from 5% to 70%, more preferably from 10% to 50%, most preferably from 15% to 45% by weight, water and/or non-aminofunctional organic solvent.

As used herein, "non-aminofunctional organic solvent" refers to any organic solvent which contains no amino functional groups. Preferred non-aminofunctional organic solvents include monohydric alcohols, dihydric alcohols, polyhydric alcohols, glycerol, glycols, polyalkylene glycols such as polyethylene glycol, and mixtures thereof. Highly preferred are mixtures of solvents, especially mixtures of two or more of the following: lower aliphatic alcohols such as ethanol, propanol, butanol, isopropanol; diols such as 1,2-propanediol or 1,3-propanediol; and glycerol. Also preferred are propanediol and mixtures thereof with diethylene glycol where the mixture contains no methanol or ethanol. Thus embodiments of fluid detergent compositions of the present invention may include embodiments in which propanediols are used but methanol and ethanol are not used.

Preferable non-aminofunctional organic solvents are liquid at ambient temperature and pressure (i.e. 21° C. and 1 atmosphere), and comprise carbon, hydrogen and oxygen. Non-aminofunctional organic solvents may be present when preparing a premix of the external structuring system, or in the final fluid detergent composition.

Adjuncts Ingredients:

The fluid detergent composition of the present invention may also include conventional detergent ingredients selected from the group consisting of: cationic surfactants, amphoteric and/or zwitterionic surfactants, non-aminofunctional organic solvents, enzymes, enzyme stabilizers, amphiphilic alkoxylated grease cleaning polymers, clay soil cleaning polymers, soil release polymers, soil suspending polymers, bleaching systems, optical brighteners, hueing dyes, particulate material, perfume and other odour control agents, hydrotropes, suds suppressors, fabric care benefit agents, pH adjusting agents, dye transfer inhibiting agents, preservatives, non-fabric substantive dyes and mixtures thereof. Some of the optional ingredients which can be used are described in greater detail as follows:

1. Additional Surfactants

The fluid detergent compositions of the present invention may comprise additional surfactant selected from the group consisting: anionic, cationic, nonionic, amphoteric and/or zwitterionic surfactants and mixtures thereof.

Cationic surfactants: Suitable cationic surfactants can be water-soluble, water-dispersable or water-insoluble. Such cationic surfactants have at least one quaternized nitrogen and at least one long-chain hydrocarbyl group. Compounds comprising two, three or even four long-chain hydrocarbyl groups are also included. Examples include alkyltrimethylammonium salts, such as C12 alkyltrimethylammonium chloride, or their hydroxyalkyl substituted analogs. Compositions known in the art may comprise, for example, 1% or more of cationic surfactants.

Amphoteric and/or zwitterionic surfactants: Suitable amphoteric or zwitterionic detersive surfactants of use in the fluid detergent compositions of the present invention include those which are known for use in hair care or other personal care cleansing. Non-limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric detersive surfactants suitable for use in the composition include those surfactants broadly described as derivatives of aliphatic secondary and tertiary amines in which the aliphatic radical can be straight or branched chain and wherein one of the aliphatic substituents contains from 8 to 18 carbon atoms and one contains an anionic group such as carboxy, sulfonate, sulfate, phosphate, or phosphonate. Suitable amphoteric detersive surfactants for use in the present invention include, but are not limited to: cocoamphoacetate, cocoamphodiacetate, lauroamphoacetate, lauroamphodiacetate, and mixtures thereof.

Zwitterionic detersive surfactants suitable for use in the compositions are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from 8 to 18 carbon atoms and one contains an anionic group such as carboxy, sulfonate, sulfate, phosphate or phosphonate. Zwitterionics such as betaines are suitable for this invention.

Furthermore, amine oxide surfactants having the formula: $R(EO)_x(PO)_y(BO)_zN(O)(CH_2R')_2 \cdot qH_2O$ (I) are also useful in compositions of the present invention. R is a relatively long-chain hydrocarbyl moiety which can be saturated or unsaturated, linear or branched, and can contain from 8 to 20, preferably from 10 to 16 carbon atoms, and is more preferably C12-C16 primary alkyl. R' is a short-chain moiety preferably selected from hydrogen, methyl and $—CH_2OH$. When $x+y+z$ is different from 0, EO is ethyleneoxy, PO is propyleneneoxy and BO is butyleneoxy. Amine oxide surfactants are illustrated by C12-C14 alkyldimethyl amine oxide.

Non-limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

2. Enzymes

The fluid detergent compositions of the present invention may comprise from 0.0001% to 8% by weight of a detersive enzyme which provides cleaning performance and/or fabric care benefits. Such compositions have a neat pH of from 6 to 10.5. Suitable enzymes include proteases, amylases, cellulases, lipases, xylogucanases, pectate lyases, mannanases, bleaching enzymes, cutinases, and mixtures thereof. A preferred enzyme combination comprises a cocktail of conventional detersive enzymes such as lipase, protease, cellulase and amylase. Detersive enzymes are described in greater detail in U.S. Pat. No. 6,579,839.

For the enzymes, accession numbers or IDs shown in parentheses refer to the entry numbers in the databases Genbank, EMBL and Swiss-Prot. For any mutations standard 1-letter amino acid codes are used with a * representing a deletion. Accession numbers prefixed with DSM refer to microorgansims deposited at Deutsche Samlung von Mikroorganismen and Zellkulturen GmbH, Mascheroder Weg 1b, 38124 Brunswick (DSMZ).

Protease: The composition may comprise a protease. Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus*, *Bacillus alkalophilus* (P27963, ELYA_BACAO), *Bacillus subtilis*, *Bacillus amyloliquefaciens* (P00782, SUBT_BACAM), *Bacillus pumilus* (P07518) and *Bacillus gibsonii* (DSM14391).

(b) trypsin-type or chymotrypsin-type proteases, such as trypsin (e.g. of porcine or bovine origin), including the Fusarium protease and the chymotrypsin proteases derived from Cellumonas (A2RQE2).

(c) metalloproteases, including those derived from *Bacillus amyloliquefaciens* (P06832, NPRE_BACAM).

Preferred proteases include those derived from *Bacillus gibsonii* or *Bacillus Lentus* such as subtilisin 309 (P29600) and/or DSM 5483 (P29599).

Suitable commercially available protease enzymes include: those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase® and Purafect OXP® by Genencor International; those sold under the tradename Opticlean® and Optimase® by Solvay Enzymes; those available from Henkel/Kemira, namely BLAP (P29599 having the following mutations S99D+S101 R+S103A +V104I+G159S), and variants thereof including BLAP R (BLAP with S3T+V4I+V199M+ V205I+L217D), BLAP X (BLAP with S3T+V4I+V205I) and BLAP F49 (BLAP with S3T+V4I+A194P+V199M+ V205I+L217D) all from Henkel/Kemira; and KAP (*Bacillus alkalophilus* subtilisin with mutations A230V+S256G+ S259N) from Kao.

Since certain di-amido gellants may be hydrolyzed by protease enzymes, it is preferred that the protease enzyme is inhibited, such as through the use of a suitable enzyme stabilizer, unless the protease enzyme is encapsulated.

Amylase: Suitable amylases are alpha-amylases, including those of bacterial or fungal origin. Chemically or genetically modified mutants (variants) are included. A preferred alkaline alpha-amylase is derived from a strain of *Bacillus*, such as *Bacillus licheniformis*, *Bacillus amyloliquefaciens*, *Bacillus stearothermophilus*, *Bacillus subtilis*, or other *Bacillus* sp., such as *Bacillus* sp. NCIB 12289, NCIB 12512, NCIB 12513, sp 707, DSM 9375, DSM 12368, DSMZ no. 12649, KSM AP1378, KSM K36 or KSM K38. Preferred amylases include:

(a) alpha-amylase derived from *Bacillus licheniformis* (P06278, AMY_BACLI), and variants thereof, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

(b) AA560 amylase (CBU30457, HD066534) and variants thereof, especially the variants with one or more substitutions in the following positions: 26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with the wild-type enzyme from *Bacillus* SP722 (CBU30453, HD066526), especially variants with deletions in the 183 and 184 positions.

Suitable commercially available alpha-amylases are Duramyl®, Liquezyme® Termamyl®, Termamyl Ultra®, Natalase®, Supramyl®, Stainzyme®, Stainzyme Plus®, Fungamyl® and BAN® (Novozymes A/S), Bioamylase® and variants thereof (Biocon India Ltd.), Kemzym® AT 9000 (Biozym Ges. m.b.H, Austria), Rapidase® , Purastar®, Optisize HT Plus®, Enzysize®, Powerase® and Purastar Oxam®, Maxamyl® (Genencor International Inc.) and KAM® (KAO, Japan). Preferred amylases are Natalase®, Stainzyme® and Stainzyme Plus®.

Cellulase: The composition may comprise a cellulase. Suitable cellulases include those of bacterial or fungal origin. Chemically modified-or protein engineered mutants are included. Suitable cellulases include cellulases from the genera *Bacillus*, *Pseudomonas*, *Humicola*, *Fusarium*, *Thielavia*, *Acremonium*, e.g., the fungal cellulases produced from *Humicola insolens*, *Myceliophthora thermophila* and *Fusarium oxysporum*.

Commercially available cellulases include Celluzyme®, and Carezyme® (Novozymes A/S), Clazinase®, and Puradax HA® (Genencor International Inc.), and KAC-500(B)® (Kao Corporation).

In one aspect, the cellulase can include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403) and mixtures thereof. Suitable endoglucanases are sold under the tradenames Celluclean® and Whitezyme® (Novozymes A/S, Bagsvaerd, Denmark).

Preferably, the composition comprises a cleaning cellulase belonging to Glycosyl Hydrolase family 45 having a molecular weight of from 17 kDa to 30 kDa, for example the endoglucanases sold under the tradename Biotouch® NCD, DCC and DCL (AB Enzymes, Darmstadt, Germany).

Highly preferred cellulases also exhibit xyloglucanase activity, such as Whitezyme®.

Lipase: The composition may comprise a lipase. Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*), or from *H. insolens*, a *Pseudomonas* lipase, e.g., from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g., from *B. subtilis, B. stearothermophilus* or *B. pumilus*.

The lipase may be a "first cycle lipase", preferably a variant of the wild-type lipase from Thermomyces lanuginosus comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex®, Lipolex® and Lipoclean® by Novozymes, Bagsvaerd, Denmark.

Preferably, the composition comprises a variant of Thermomyces lanuginosa (O59952) lipase having >90% identity with the wild type amino acid and comprising substitution(s) at T231 and/or N233, preferably T231R and/or N233R.

In another aspect, the composition comprises a variant of *Thermomyces lanuginosa* (O59952) lipase having >90% identity with the wild type amino acid and comprising substitution(s):

(a) S58A+V60S+I83T+A150G+L227G+T231R+N233R+I255A+P256K;
(b) S58A+V60S+I86V+A150G+L227G+T231R+N233R+I255A+P256K;
(c) S58A+V60S+I86V+T143S+A150G+L227G+T231R+N233R+I255A+P256K;
(d) S58A+V60S+I86V+T143S+A150G+G163K+S216P+L227G+T231R+N233R+I255A+P256K;
(e) E1*+S58A+V69S+I86V+T143S+A150G+L227G+T231R+N233R+I255A+P256K;
(f) S58A+V60S+I86V+K98I+E99K+T143S+A150G+L227G+T231R+N233R+I255A+P256K;
(g) E1N+S58A+V60S+I86V+K98I+E99K+T143S+A150G+L227G+T231R+N233R+I255A+P256K+L259F;
(h) S58A+V60S+I86V+K98I+E99K+D102A+T143S+A150G+L227G+T231R+N233R+I255A+P256K;
(i) N33Q+S58A+V60S+I86V+T143S+A150G+L227G+T231R+N233R+I255A+P256K;
(j) E1*+S58A+V60S+I86V+K98I+E99K+T143S+A150G+L227G+T231R+N233R+I255A+P256K;
(k) E1N+S58A+V60S+I86V+K98I+E99K+T143S+A150G+S216P+L227G+T231R+N233R+I255A+P256K;
(l) D27N+S58A+V60S+I86V+G91N+N94R+D1UN+T143S+A150G+L227G+T231R+N233R+I255A+P256K;
(m) E1N+S58A+V60S+I86V+K98I+E99K+T143S+A150G+E210A+S216P+L227G+T231R+N233R+I255A+P256K;
(n) A150G+E210V+T231R+N233R+I255A+P256K; and
(o) I202L+E210G+T231R+N233R+I255A+P256K.

When lipase is present, it is preferred that the di-amido gellant comprises no ester-bonds, since some di-amido gellants that comprise ester-bonds may be hydrolyzed by the lipase enzyme, unless the lipase enzyme is encapsulated.

Xyloglucanase: Suitable xyloglucanase enzymes have enzymatic activity towards both xyloglucan and amorphous cellulose substrates, wherein the enzyme is a glycosyl hydrolase (GH) is selected from GH families 5, 12, 44 or 74. Preferably, the glycosyl hydrolase is selected from GH family 44. Suitable glycosyl hydrolases from GH family 44 are the XYG1006 glycosyl hydrolase from Paenibacillus polyxyma (ATCC 832) and variants thereof.

Pectate lyase: Suitable pectate lyases are either wild-types or variants of *Bacillus*-derived pectate lyases (CAF05441, AAU25568) sold under the tradenames Pectawash®, Pectaway® and X-Pect® (from Novozymes A/S, Bagsvaerd, Denmark).

Mannanase: Suitable mannanases are sold under the tradenames Mannaway® (from Novozymes AJS, Bagsvaerd, Denmark), and Purabrite® (Genencor International Inc., Palo Alto, Calif.).

Bleaching enzyme: Suitable bleach enzymes include oxidoreductases, for example oxidases such as glucose, choline or carbohydrate oxidases, oxygenases, catalases, peroxidases, like halo-, chloro-, bromo-, lignin-, glucose- or manganese-peroxidases, dioxygenases or laccases (phenoloxidases, polyphenoloxidases). Suitable commercial products are sold under the Guardzyme® and Denilite® ranges from Novozymes. Advantageously, additional, preferably organic, particularly preferably aromatic compounds are incorporated with the bleaching enzyme; these compounds interact with the bleaching enzyme to enhance the activity of the oxidoreductase (enhancer) or to facilitate the electron flow (mediator) between the oxidizing enzyme and the stain typically over strongly different redox potentials.

Other suitable bleaching enzymes include perhydrolases, which catalyse the formation of peracids from an ester substrate and peroxygen source. Suitable perhydrolases include variants of the Mycobacterium smegmatis perhydrolase, variants of so-called CE-7 perhydrolases, and variants of wild-type subtilisin Carlsberg possessing perhydrolase activity.

Cutinase: Suitable cutinases are defined by E.C. Class 3.1.1.73, preferably displaying at least 90%, or 95%, or most preferably at least 98% identity with a wild-type derived from one of Fusarium solani, Pseudomonas Mendocina or Humicola Insolens.

Identity: The relativity between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

Enzymes, particularly protease and lipase, may be encapsulated. Suitable encapsulated enzymes may be prepared by methods such as:
 (i) interfacial condensation polymerization, including capsules formed by the reaction of acid chlorides with compounds containing at least two amine groups and polycondensation reaction of formaldehyde with melamine. Examples of such methods are disclosed in U.S. Pat. Nos. 4,906,396, 6,221,829, 6,359,031, 6,242,405 and WO 07/100501 A2.
 (ii) sol-gel processes including capsules made by reaction of aminoalkylsilane precursors and aminoalkyl-trialkoxysilane, and one or more alkoxysilane precursors, examples of which are disclosed in WO 05/028603 A1 and WO 05/028604 A1; and
 (iii) polyelectrolyte precipitation, including capsules formed by reaction of chitosan and alginate or using biopolymer gels such as gellan. Examples of such methods are disclosed in EP 1,502,645 A1.

(iv) Spray drying, including capsules derived from spray drying mixtures comprising at least one cellulosic polymer selected from the group consisting of hydroxypropyl methylcellulose phthalate (HPMCP), cellulose acetate phthalate (CAP), and mixtures thereof. Such polymers include polymers that are commercially available under the trade names NF Hypromellose Phthalate (HPMCP) (Shin-Etsu), cellulose ester NF or cellulose cellacefate NF (CAP) from G. M. Chemie Pvt Ltd, Mumbai, 400705, India and Eastman Chemical Company, Kingsport, USA. Examples of such methods are disclosed in WO/2011/005943.

The encapsulated protease may comprise at least 0.5%, or at least 1%, or at least 2%, or at least 5%, or at least 10%, or even at least 20% by weight active protease enzyme.

Encapsulated proteases may comprise from about 5% to about 90% active protease by weight.

Encapsulated proteases may be incorporated into the compositions of the present invention, based on total cleaning composition weight, at a level of from 0.001% to about 30%, or from about 0.005% to about 25%, or from about 0.05% to about 10% or even from about 0.01% to about 2%.

Without wishing to be bound by theory, it is believed that having a low particle size facilitates the liquid phase's ability to suspend the particles, thereby keeping the liquid phase as homogenous as possible. When said encapsulated proteases are in the form of enzyme microcapsules, said microcapsules typically have a particle size of from about 100 microns to about 0.05 microns, from about 80 microns to about 0.05 microns, or even from about 50 microns to about 0.05 microns. Thus, in one aspect, such microcapsules are sized such that they are not typically visible to a consumer when such microcapsules are incorporated into a cleaning composition.

Preferably, the encapsulated protease releases at least 80% of its protease load within 10 minutes, within 5 minutes, or even within 2 minutes upon dilution in the wash. These release rates are preferably achievable at ambient temperatures under a 100 fold dilution at 20° C. with stirring at 150 rpm. Protease activity can be determined by any standard method such as use of protease analysis kits available from Sigma Aldrich, Milwaukee, Wis., USA or ASTM method D0348-89 (2003). Without wishing to be bound by theory, it is believed that a better cleaning profile is obtained as the time that the enzymes have to interact with the soil is increased.

Encapsulated proteases may be enzyme granulates/prills, having an average particle size of 200-1000 microns. Such enzyme granulates/prills may be made in accordance with the teachings of U.S. Pat. Nos. 4,106,991, 4,242,219, 4,689,297, 5,324,649 and 7,018,821 B2. In one aspect, such enzyme granulates/prills may comprise a dye and/or pigment. In one aspect, such enzyme granulates/prills may comprise a coating comprising hydroxypropylmethylcellulose and/or polyvinylalcohol and derivatives thereof.

3. Enzyme Stabilizers

Suitable mass efficient reversible protease inhibitors for the inhibition of serine proteases would include derivates of boronic acid, especially derivatives of phenyl boronic acid and peptide aldehydes, including tripeptide aldehydes. Examples of such compounds are disclosed in WO 98/13458 A1, WO 07/113241 A1, and U.S. Pat. No. 5,972,873.

The stabilizer may be selected from the group consisting of thiophene-2 boronic acid, thiophene-3 boronic acid, acetamidophenyl boronic acid, benzofuran-2 boronic acid, naphtalene-1 boronic acid, naphtalene-2 boronic acid, 2-fomyl phenyl boronic acid (2-FPBA), 3-FBPA, 4-FBPA, 1-thianthrene boronic acid, 4-dibenzofuran boronic acid, 5-methylthiophene-2 boronic, acid, thionaphtrene boronic acid, furan-2 boronic acid, furan-3 boronic acid, 4,4-biphenyldiboronic acid, 6-hydroxy-2-naphtalene, 4-(methylthio) phenyl boronic acid, 4-(trimethylsilyl)phenyl boronic acid, 3-bromothiophene boronic acid, 4-methylthiophene boronic acid, 2-naphtyl boronic acid, 5-bromothiphene boronic acid, 5-chlorothiophene boronic acid, dimethylthiophene boronic acid, 2-bromophenyl boronic acid, 3-chlorophenyl boronic acid, 3-methoxy-2-thiophene, p-methyl-phenylethyl boronic acid, 2-thianthrene boronic acid, di-benzothiophene boronic acid, 4-carboxyphenyl boronic acid, 9-anthryl boronic acid, 3,5-dichlorophenyl boronic, acid, diphenyl boronic acidanhydride, o-chlorophenyl boronic acid, p-chlorophenyl boronic acid m-bromophenyl boronic acid, p-bromophenyl boronic acid, p-fluorophenyl boronic acid, p-tolyl boronic acid, o-tolyl boronic acid, octyl boronic acid, 1,3,5-trimethylphenyl boronic acid, 3-chloro-4-flourophenyl boronic acid, 3-aminophenyl boronic acid, 3,5-bis-(trifluoromethyl)phenyl boronic acid, 2,4 dichlorophenyl boronic acid, 4-methoxyphenyl boronic acid and mixtures thereof. Further suitable boronic acid derivatives suitable as stabilizers are described in U.S. Pat. Nos. 4,963,655, 5,159,060, WO 95/12655, WO 95/29223, WO 92/19707, WO 94/04653, WO 94/04654, U.S. Pat. Nos. 5,442,100, 5,488,157 and 5,472,628.

Suitable mass efficient reversible protease inhibitors may comprise 4-formyl phenyl boronic acid.

The mass efficient reversible protease inhibitor may comprise a reversible peptide protease inhibitor. Examples of suitable reversible peptide protease inhibitors and processes for making same may be found in U.S. Pat. No. 6,165,966 and WO 98/13459 A1.

Suitable tripeptide enzyme inhibitors may have the following structure:

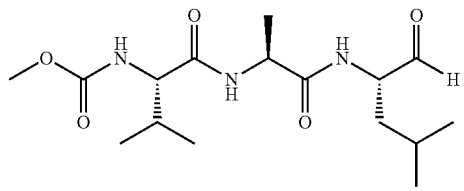

The mass efficient reversible protease inhibitor may comprise a protease inhibitor of the protein type such as RASI, BASI, WASI (bifunctional alpha-amylase/subtilisin inhibitors of rice, barley and wheat) as disclosed in WO09/095425 or SSI (streptomyces subtilisin inhibitor) and variants thereof as disclosed in Protein Engineering Design & Selection, vol 17 no. 4, p. 333-339, 2004.

4. Polymer Deposition Aids

Preferably, the fluid detergent composition comprises from 0.1% to 7%, more preferably from 0.2% to 3%, of a polymer deposition aid. As used herein, "polymer deposition aid" refers to any cationic polymer or combination of cationic polymers that significantly enhance deposition of a fabric care benefit agent onto substrates (such as fabric) during washing (such as laundering). Suitable polymer deposition aids can comprise a cationic polysaccharide and/or a copolymer. "Fabric care benefit agent" as used herein refers to any material that can provide fabric care benefits. Non-limiting examples of fabric care benefits include, but are not limited to: fabric softening, color protection, color restoration, pill/fuzz reduction, anti-abrasion and anti-wrinkling. Non-limiting examples of fabric care benefit agents include: silicone derivatives, oily sugar derivatives, dispersible polyolefins, polymer latexes, cationic surfactants and combinations thereof.

5. Cleaning Polymers

The detergent compositions herein may optionally contain from 0.01 to 10% by weight of one or more cleaning polymers that provide for broad-range soil cleaning of surfaces and fabrics and/or suspension of the soils. Any suitable cleaning polymer may be of use. Useful cleaning polymers are described in US 2009/0124528A1. Non-limiting examples of useful categories of cleaning polymers include: amphiphilic alkoxylated grease cleaning polymers; clay soil cleaning polymers; soil release polyers; and soil suspending polymers.

6. Bleaching Systems

One embodiment is a composition, wherein the composition is a fluid laundry bleach additive comprising from 0.1% to 12% by weight of a bleach or bleach system, preferably a peroxide bleach, and further comprises a neat pH of from 2 to 6. Another embodiment is a fluid laundry detergent composition comprising: from 0.1% to 12% by weight of the bleach, and a neat pH of from 6.5 to 10.5. Suitable hydrogen peroxide sources are described in detail in Kirk Othmer's Encyclopaedia of Chemical Technology, 4th Ed (1992, John Wiley & Sons), Vol. 4, pp. 271-300 "Bleaching Agents (Survey)", and include the various forms of sodium perborate and sodium percarbonate, including various coated and modified forms. For example, hydrogen peroxide itself; perborates, e.g., sodium perborate (any hydrate but preferably the mono- or tetra-hydrate); sodium carbonate peroxyhydrate or equivalent percarbonate salts; sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Compositions of the present invention may also comprise as the bleaching agent a chlorine-type bleaching material. Such agents are well known in the art, and include for example sodium dichloroisocyanurate ("NaDCC"). However, chlorine-type bleaches are less preferred for compositions comprising enzymes. They bleaching systems of use in the present invention may also include ingredients selected from the group consisting of: bleach activators, hydrogen peroxide, hydrogen peroxide sources, organic peroxides, metal-containing bleach catalysts, transition metal complexes of macropolycyclic rigid ligands, other bleach catalysts, preformed peracids, photobleaches and mixtures thereof.

Bleach Activators: The peroxygen bleach component in the composition can be formulated with an activator (peracid precursor), present at levels of from 0.01 to 15%, preferably from 0.5 to 10%, more preferrably from 1% to 8% by weight of the composition. Preferred activators are selected from the group consisting of: tetraacetyl ethylene diamine (TAED), benzoylcaprolactam (BzCL), 4-nitrobenzoylcaprolactam, 3-chlorobenzoylcaprolactam, benzoyloxybenzeneulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, alternatively benzoylcaprolactam and benzoylvalerolactam, 4-[N-(nonaoyl) amino hexanoyloxy]-benzene sulfonate sodium salt (NACA-OBS) (See U.S. Pat. No. 5,523,434), dodecanoyloxy-benzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA) and mixtures thereof.

Non-limiting examples of suitable bleach activators, including quaternary substituted bleach activators, are described in U.S. Pat. No. 6,855,680.

Hydrogen Peroxides sources: Suitable examples include inorganic perhydrate salts, including alkali metal salts such as sodium salts of perborate (usually mono- or tetra-hydrate), percarbonate, persulphate, perphosphate, persilicate salts and mixtures thereof. When employed, inorganic perhydrate salts are typically present in amounts of from 0.05% to 40%, preferably from 1% to 30% by weight of the composition.

Organic Peroxides: Diacyl Peroxides that do not cause visible spotting or filming are particularly preferred. One example is dibenzoyl peroxide. Other suitable examples are illustrated in Kirk Othmer, Encyclopedia of Chemical Technology at 27-90, v. 17, John Wiley and Sons, (1982).

Metal-containing Bleach Catalysts: Preferred bleach catalysts include manganese and cobalt-containing bleach catalysts. Other suitable metal-containing bleach catalysts include catalyst systems comprising a transition metal cation of defined bleach catalytic activity, such as copper, iron, titanium, ruthenium tungsten, molybdenum, or manganese cations; an auxiliary metal cation having little or no bleach catalytic activity, such as zinc or aluminum cations; and a sequestrate having defined stability constants for the catalytic and auxiliary metal cations, particularly ethylenediaminetetraacetic acid, ethylenediaminetetra(methylenephosphonic acid) and water-soluble salts thereof. Suitable catalyst systems are disclosed in U.S. Pat. No. 4,430,243.

Transition Metal Complexes of Macropolycyclic Rigid Ligands: The fluid detergent compositions herein may also include bleach catalysts comprising a transition metal complex of a macropolycyclic rigid ligand. The amount used is preferably more than 1 ppb, more preferably 0.001 ppm or more, even more preferably from 0.05 ppm to 500 ppm (wherein "ppb" denotes parts per billion by weight and "ppm" denotes parts per million by weight).

Other Bleach Catalysts: Other bleach catalysts such as organic bleach catalysts and cationic bleach catalysts are suitable for the fluid detergent compositions of the invention. Organic bleach catalysts are often referred to as bleach boosters. The fluid detergent compositions herein may comprise one or more organic bleach catalysts to improve low temperature bleaching. Preferred organic bleach catalysts are zwitterionic bleach catalysts, including aryliminium zwitterions. Suitable examples include 3-(3,4-dihydroisoquinolinium) propane sulfonate and 3,4-dihydro-2-[2-(sulfooxy)decyl]isoquinolimium. Suitable aryliminium zwitterions include:

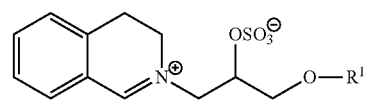

wherein $R^1$ is a branched alkyl group containing from 9 to 24 carbons or linear alkyl group containing from 11 to 24 carbons. Preferably, each $R^1$ is a branched alkyl group containing from 9 to 18 carbons or linear alkyl group containing from 11 to 18 carbons, more preferably each $R^1$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other suitable examples of organic bleach catalysts can be found in U.S. Pat. Nos. 5,576,282 and 5,817,614, EP 923,636 B1, WO 2001/16263 A1, WO 2000/42156 A1, WO 2007/001262 A1.

Suitable examples of cationic bleach catalysts are described in U.S. Pat. Nos. 5,360,569, 5,442,066, 5,478,357, 5,370,826, 5,482,515, 5,550,256, WO 95/13351, WO 95/13352, and WO 95/13353.

Preformed peracids: The preferred preformed peracid is Phthalimido peroxycaproic acid (PAP). Other suitable preformed peracids include, but are not limited to, compounds selected from the group consisting of: percarboxylic acids and salts, percarbonic acids and salts, perimidic acids and salts, peroxymonosulfuric acids and salts, and mixtures thereof. In compositions such as bleach containing fluid laundry detergents, the preformed peracid may be present at a level of from 0.1% to 25%, preferably from 0.5% to 20%, more preferably from 1% to 10%, most preferably from 2% to 4% by weight of the composition. Alternatively, higher levels of peracid may be present. For instance, compositions such as fluid laundry bleach additives may comprise from 10% to 40%, preferably from 15% to 30%, more preferably from 15% to 25% by weight preformed peracid.

7. Optical Brighteners

These are also known as fluorescent whitenening agents for textiles. Preferred levels are from 0.001% to 1% by weight of the fluid detergent composition. Suitable brighteners are disclosed in EP 686691B and include hydrophobic as well as hydrophilic types. Brightener 49 is preferred for use in the present invention.

8. Hueing Dyes

Hueing dyes or fabric shading dyes are useful adjuncts in fluid detergent compositions. Suitable dyes include blue and/or violet dyes having a hueing or shading effects. The fluid detergent compositions herein may comprise from 0.00003% to 0.1%, preferably from 0.00008% to 0.05%, more preferably from 0.0001% to 0.04% by weight of the fabric hueing dye.

9. Particulate Material

The fluid detergent composition may include particulate material such as clays, suds suppressors, encapsulated sensitive ingredients, e.g., perfumes including perfume microcapsules, bleaches and enzymes in encapsulated form; or aesthetic adjuncts such as pearlescent agents including mica, pigment particles, or the like. Suitable levels are from 0.0001% to 5%, or from 0.1% to 1% by weight of the fluid detergent composition.

10. Perfume and Odour Control Agents

In preferred embodiments, the fluid detergent composition comprises a perfume. If present, perfume is typically incorporated at a level from 0.001 to 10%, preferably from 0.01% to 5%, more preferably from 0.1% to 3% by weight of the composition. The perfume may comprise a perfume microcapsule and/or a perfume nanocapsule. In other embodiments, the fluid detergent composition comprises odour control agents such as uncomplexed cyclodextrin as described in U.S. Pat. No. 5,942,217.

11. Hydrotropes

The fluid detergent composition optionally comprises a hydrotrope in an effective amount, i.e. up to 15%, preferably 1% to 10%, more preferably 3% o 6% by weight, so that the fluid detergent compositions are compatible in water. Suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof, as disclosed in U.S. Pat. No. 3,915,903.

Unit Dose Detergent:

In some embodiments of the present invention, the fluid detergent composition is enclosed within a water soluble pouch material. Preferred polymers, copolymers or derivatives thereof suitable for in pouch materials are selected from the group: polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof.

Process of Making:

The present invention also provides for a preferred process of making a fluid detergent composition comprising the steps of (i) providing a structurant premix comprising a di-amido gellant, and (ii) combining the structurant premix with a detergent feed, said detergent feed comprising an anionic and/or nonionic surfactant. Step (i) and step (ii) may both include an anionic surfactant. The anionic surfactants used in these steps can be the same or different. In another embodiment, the structurant premix further comprises a secondary external structurant. In yet another embodiment, the second external structurant is provided in the detergent feed. Providing the premix may comprise a step of forming a premix. It has been found that the premix can be free or essentially free of water. For instance, in one embodiment, the structurant premix comprises a solvent, preferably an organic solvent, to solubilise the di-amido gellant. This is a substantial advantage when structuring fluid detergent compositions that are either highly concentrated and/or comprise very little water (less than 20%, preferably less than 10% by weight water). For instance, fluid detergent compositions packaged in water-soluble pouch materials. The premix may also be free or essentially free of added electrolytes. The organic solvent is preferably selected from the group consisting of: an organic solvent, a nonionic surfactant, an anionic surfactant, or mixtures thereof.

In another embodiment, the process comprises the additional step of (iii) cooling the composition of step (ii). In yet another embodiment, the process comprises the additional step of adding heat sensitive ingredients such as detersive enzymes when the step of cooling the composition brings the compositional temperature below the temperature where the heat sensitive ingredients are subject to decomposition.

In one embodiment, the step of forming the structurant premix is performed at a temperature above which the said di-amido gellant dissolves in the solvent (for instance above 80° C., alternatively above 95° C.). Preferably, the temperature at which the premix is formed is at least 5° C., more preferably at least 10° C. higher than the temperature at which all the di-amido gellant is fully dissolved in the premix.

In another embodiment, the step of combining the structurant premix with the detergent feed is performed by adding the structurant premix at a temperature of at least 80° C., to the detergent feed heated up to a temperature of not more than 60 ° C., preferably not more than 50° C. The heat-sensitive ingredients, such as enzymes, perfumes, bleach catalysts, photobleaches, bleaches and dyes are preferably added to the detergent feed after the structurant premix has been added, and after the temperature is below 45° C., preferably below 30° C.

Test Methods:
1. Turbidity (NTU):

The turbidity (measured in NTU: Nephelometric Turbidity Units) is measured using a Hach 2100P turbidity meter calibrated according to the procedure provided by the manufacture. The sample vials are filled with 15 ml of representative sample and capped and cleaned according to the operating instructions. If necessary, the samples are degassed to remove any bubbles either by applying a vacuum or using an ultrasonic bath (see operating manual for procedure). The turbidity is measured using the automatic range selection.

2. Minimum Gelling Concentration (MGC)

MGC is calculated by a tube inversion method based on R. G. Weiss, P. Terech; "Molecular Gels: Materials with self-assembled fibrillar structures" 2006 springer, p 243. In order to determine the MGC, three screenings are done:
- a) First screening: prepare several vials increasing the di-amido gellant concentration from 0.5% to 5.0 weight % in 0.5% steps
- b) Determine in which interval the gel is formed (one inverted sample still flowing and the next one is already a strong gel). In case no gel is formed at 5%, higher concentrations are used.
- c) Second screening: prepare several vials increasing the di-amido gellant concentration in 0.1 weight % steps in the interval determined in the first screening.
- d) Determine in which interval the gel is formed (one inverted sample still flowing and the next one is already a strong gel)
- e) Third screening: in order to have a very precise percentage of the MGC, run a third screening in 0.025 weight % steps in the interval determined in the second screening.
- f) The Minimum Gelling Concentration (MGC) is the lowest concentration which forms a gel in the third screening (does not flow on inversion of the sample).

For each screening, samples are prepared and treated as follows: 8mL vials (Borosilacate glass with Teflon cap, ref. B7857D, Fisher Scientific Bioblock) are filled with 2.0000±0.0005 g (KERN ALJ 120-4 analytical balance with ±0.1 mg precision) of the fluid (comprising the fluid detergent composition and di-amido gellant) for which we want to determine the MGC. The vial is sealed with the screw cap and left for 10 minutes in an ultrasound bath (Elma Transsonic T 710 DH, 40 kHz, 9.5 L, at 25° C. and operating at 100% power) in order to disperse the solid in the liquid. Complete dissolution is then achieved by heating, using a heating gun (Bosch PHG-2), and gentle mechanical stirring of the vials. It is crucial to observe a completely clear solution. Handle vials with care. While they are manufactured to resist high temperatures, a high solvent pressure may cause the vials to explode. Vials are cooled to 25° C., for 10 min in a thermostatic bath (Compatible Control Thermostats with controller CC2, D77656, Huber). Vials are inverted, left inverted for 1 minute, and then observed for which samples do not flow. After the third screening, the concentration of the sample that does not flow after this time is the MGC. For those skilled in the art, it is obvious that during heating solvent vapours may be formed, and upon cooling down the samples, these vapours can condense on top of the gel. When the vial is inverted, this condensed vapour will flow. This is discounted during the observation period. If no gels are obtained in the concentration interval, higher concentrations must be evaluated.

3. Rheology

An AR-G2 rheometer from TA Instruments is used for rheological measurements.

Figure 2:
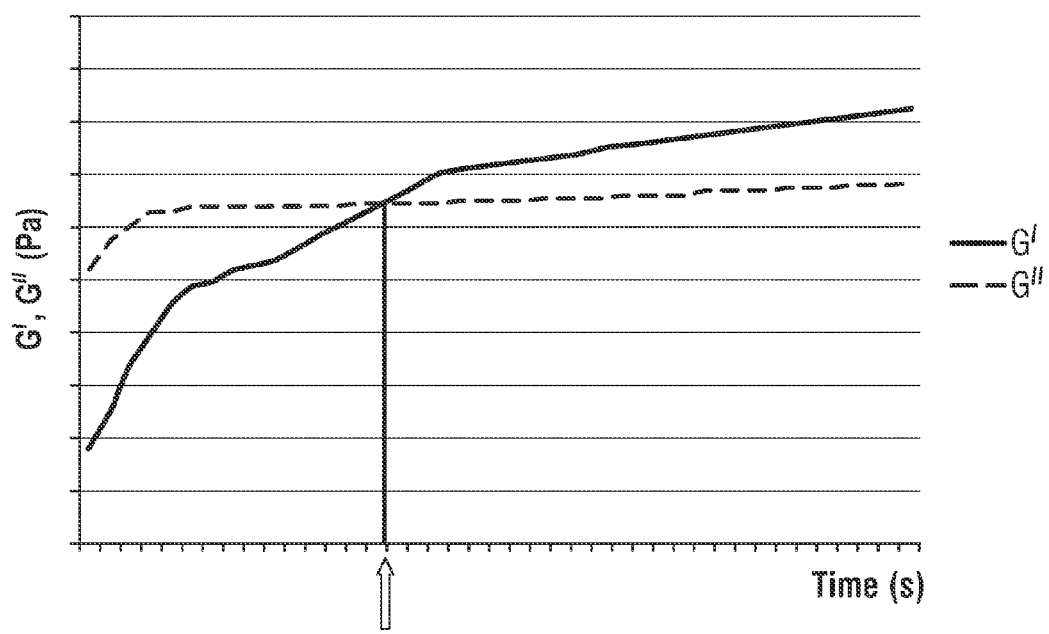
FIG. 2 details G' and G" cross over as a measure of restructuring kinetics.

Plate: 40 mm standard steel parallel plate, 300 μm gap.
1. Gel strength: The gel strength is measured using a stress sweep test whereby the oscillation stress is increased from 0.001 Pa to 10 Pa, taking 10 points per decade at 20° C. and at a frequency of 1 Hz. We use G' and G" within the linear viscoelastic region and the oscillation stress at the point where G' and G" cross over as a measure for the gel strength, as shown in FIG. 1.
2. Recovery of structure: first we apply a pre-shear of 30 s-1 at 20° C. for 60 s, after which we follow how the structure recovers applying a time sweep test with an oscillation stress of 0.02 Pa and a single frequency of 1 Hz at 20° C. for 10 minutes. As a measure of the restructuring kinetics, we use G' and G" cross over, as shown in the FIG. 2.

EXAMPLES

Example 1

A Liquid Laundry Detergent Composition According to the Invention is Prepared as Follows Step 1: A structurant premix A1 is prepared by dissolving 0.20 g dibenzyl(2S,2'S)-1,1'-(propane-1,3-diylbis(azanediyl))bis(3-methyl-1-oxobutane-2,1-diyl)dicarbamate in 9.8 g solvent (1,2-propanediol).

Step 2: A detergent feed B1 comprising the temperature—insensitive ingredients and having the composition described in Table 4 is prepared.

TABLE 4

Composition of detergent feed B1

| Ingredient | Detergent Feed B1 Grams |
|---|---|
| Linear Alkylbenzene sulfonic acid (LAS) | 12.0 |
| C12-14 alkyl ethoxy 3 sulfate Mono Ethanol Amine salt | 9.3 |
| C12-14 alkyl 7-ethoxylate | 8.0 |
| Citric acid | 3.0 |
| C12-18 Fatty Acid | 10.0 |
| Grease Cleaning Alkoxylated Polyalkylenimine Polymer[1] | 0.9 |
| PEG PVAc Polymer[2] | 0.9 |
| Soil Suspending Alkoxylated Polyalkylenimine Polymer[3] | 2.2 |
| Hydroxyethane diphosphonic acid | 1.6 |
| FWA | 0.23 |
| Ethanol | 1.5 |
| Boric acid | 0.5 |
| MEA | Up to pH 8 |
| Water up to | 66 grams |

[1]600 g/mol molecular weight polyethylenimine core with 24 ethoxylate groups per —NH and 16 propoxylate groups per —NH.
[2]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is 6000 and the weight ratio of the polyethylene oxide to polyvinyl acetate is 40 to 60 and no more than 1 grafting point per 50 ethylene oxide units.
[3]600 g/mol molecular weight polyethylenimine core with 20 ethoxylate groups per —NH.

Step 3: 10 grams of structurant premix A1 heated up to 100° C. is mixed with 66 grams of detergent feed B1 heated up to 60° C. at 400 rpm for 2 min, and the resulting mixture is let to cool down.

Step 4: When the temperature has dropped below 45° C., the heat—sensitive ingredients (1.5 gram protease, 0.7 gram amylase, 0.1 gram mannanase, 0.1 gram xyloglucanase, 0.4 gram pectate lyase and 1.7 gram of perfume) and 19.5 grams of deionized water are added under gentle stirring, at 300-400 rpm for 5 min, and the detergent composition is left to cool down to room temperature without any further agitation.

TABLE 5

| | Gel strength | | | |
|---|---|---|---|---|
| Example n. | G' (Pa) | G" (Pa) | Oscillation stress (Pa) | Recovery Time (s) |
| 1 | 8.2 | 7.6 | 0.04 | 400 |

Rheology Data

Example 2

Unit Dose Laundry Detergent

A liquid laundry detergent composition according to the invention is prepared as follows:

Step 1: A structurant premix A2 is prepared by adding 0.53 g dibenzyl(2S,2'S)-1,1'-(propane-1,3-diylbis(azanediyl))bis(3-methyl-1-oxobutane-2,1-diyl)dicarbamate in 39.47 grams of 1,2 propanediol and heating the mixture under stirring to 110° C. until fully dissolved.

Step 2: A detergent feed B2 having the composition described in Table 6 is prepared.

TABLE 6

Composition of detergent feed B2

| Ingredient | Detergent Feed B2 % of base @ 100% active |
|---|---|
| 1,2-Propanediol | 10 |
| Citric Acid | 0.5 |
| MEA | 10 |
| Glycerol | 5 |
| Hydroxyethane diphosphonic acid | 1 |
| Potassium sulfite | 0.2 |
| C12-45 alkyl 7-ethoxylate | 20 |
| Linear Alkylbenzene sulfonic acid | 24.5 |
| FWA | 0.2 |
| C12-18 Fatty Acid | 16 |
| Ethoxysulfated Hexamethylene Diamine Dimethyl Quat | 2.9 |
| Soil Suspending Alkoxylated Polyalkylenimine Polymer[3] | 1 |
| MgCl$_2$ | 0.2 |
| Protease enzyme | 1.4 |
| Mannanase enzyme | 0.1 |
| Amylase enzyme | 0.2 |
| Water & minors | Up to 100% |

Step 3: 3 grams of structurant premix A2 are heated to 100° C. while detergent feed B2 is heated to 60° C. The 3 grams of structurant premix A2 are added to 37 grams of detergent feed B2.

Step 4: After mixing at 400 rpm for 2 minutes, the resulting mixture is allowed to cool to room temperature to form the fluid detergent composition.

The fluid detergent composition is then packed into a polyvinyl alcohol pouch using standard techniques horizontal form fill techniques. The water soluble film material was Monosol M-8630.

Examples 3A to 3D

A Liquid Laundry Detergent Composition According to the Invention is Prepared as Follows Step 1: The di-amido gellant premix is prepared by adding the required amount of dibenzyl (2S ,2'S)-1,1'-(propane-1,3-diylbis(azanediyl))bis(3-methyl-1-oxobutane-2,1-diyl)di-carbamate in the required amount of ethanol and heating the mixture to 77° C. until fully dissolved.

Step 2: A detergent feed is created from the remaining ingredients by the same means as Example 1 Step 2.

Step 3: The required amount of the di-amido gellant premix is heated up to 77° C. and mixed with the required amount of detergent premix at 60° C. (mixing at 400 rpm for 2 min). The resulting mixture is allowed to cool down.

TABLE 7

Fluid laundry detergent composition comprising a di-amido gellant:

| | % w/w liquid laundry detergent composition | | | |
|---|---|---|---|---|
| Component | 3A | 3B | 3C | 3D |
| C11.8 linear alkylbenzene sulfonic acid | 17.2 | 17.2 | 13.5 | 14.0 |
| Neodol 23-5 | | | 5.2 | |
| Neodol 23-9 | 10.4 | 10.4 | 5.2 | 8.4 |
| Citric acid | 5.0 | 5.0 | 4.5 | 4.1 |
| DTPA[1] | 0.3 | 0.3 | 0.2 | 0.2 |
| Ethanolamine | 3.3 | 3.3 | 2.6 | 2.6 |
| Sodium hydroxide | 0.6 | to adjust pH | to adjust pH | to adjust pH |
| ethoxylated amine polymer | 2.0 | 2.0 | 1.6 | 1.6 |
| ethanol[2] | 2.0 | 2.0 | 2.0 | 2.0 |
| silicone suds suppressor | 0.04 | 0.04 | 0.03 | 0.03 |
| Tinopal CBS-X | 0.2 | 0.2 | 0.2 | 0.2 |
| Perfume | 0.3 | 0.3 | 0.2 | 0.2 |
| Blue EM[3] | 0.005 | | | |
| Basic Violet 3 (CI 42555)[4] | | 0.005 | | |
| Basic Violet 4 (CI 42600)[5] | | | 0.001 | |
| Acid Blue 7 (CI 42080)[6] | | | 0.0003 | |
| dibenzyl (2S,2'S)-1,1'(propane-1,3-diylbis(azanediyl))bis(3-methyl-1-oxobutane-2,1-diyl)dicarbamate[7] | 0.125 | 0.250 | 0.250 | 0.250 |
| water | balance | balance | balance | balance |
| neat pH (of composition) | 3.2 | 3.2 | 2.5 | 2.7 |
| reserve acidity[8] | 2.5 | 2.5 | 2.9 | 2.5 |
| Misc | 0.1 | 0.1 | 0.1 | 0.1 |
| Balance Water | | | | |

[1]diethyleneetriaminepentaacetic acid sodium salt
[2]added via di-amido gellant premix
[3]polymeric colorant supplied by Milliken
[4,5]fabric hueing dyes
[6]non-fabric substantive dye
[7]added via di-amido gellant premix
[8]gNaOH/100 g of product Examples 4A to 4E Fluid Detergent Fabric Care Compositions Comprising Amido-Gellants of the Present Invention Fluid detergent fabric care compositions may be prepared by mixing together the ingredients listed in the proportions shown:

TABLE 8

Fluid Detergent Fabric Care Compositions comprising amido-gellants:

| Ingredient | 4A Wt % | 4B Wt % | 4C Wt % | 4D Wt % | 4E Wt % |
|---|---|---|---|---|---|
| C12-15 alkyl polyethoxylate (3.0) sulfate | 3.8 | 3.8 | 3.8 | 2.8 | 3.3 |
| C11.8 linear alkylbenzene sulfonc acid | 11 | 11 | 9.3 | 6.4 | 9.5 |
| C14-15 alkyl 7-ethoxylate | 6.7 | 6.7 | 1.9 | 2.1 | 9.5 |
| C12-14 alkyl 7-ethoxylate | 0.5 | 0.5 | 0.5 | 0.5 | 0.5 |
| 1,2 Propane diol | 4 | 3 | 4 | 4 | 4 |
| Ethanol | 1 | 1 | 1 | 1 | 1 |
| Di Ethylene Glycol | — | 2 | — | — | — |
| Na Cumene Sulfonate | 3 | 3 | 3 | 3 | 3 |
| $C_{12-18}$ Fatty Acid | 2.6 | 2.6 | 3.3 | 2.6 | 2.6 |
| Citric acid | 2.6 | 2.6 | 3.7 | 4.3 | 2.6 |
| Protease (40.6 mg/g/)[1] | 0.5 | 0.5 | 0.5 | 0.5 | 0.5 |
| Natalase 200L (29.26 mg/g)[2] | 0.1 | 0.1 | 0.1 | 0.1 | 0.1 |
| Termamyl Ultra (25.1 mg/g)[2] | 0.05 | 0.05 | 0.05 | 0.05 | 0.05 |
| Mannaway 25L (25 mg/g)[2] | 0.05 | 0.05 | 0.05 | 0.05 | 0.05 |
| Lipase (16.91 mg/g)[2] | 0.5 | — | 0.25 | — | 0.5 |
| Lipolex ®[2] | — | 0.2 | — | — | — |
| Lipex ®[2] | — | — | — | 0.25 | — |
| Whitezyme (20 mg/g)[2] | 0.05 | 0.05 | 0.05 | 0.05 | 0.05 |
| Fluorescent Whitening Agent | 0.1 | 0.1 | 0.1 | 0.1 | 0.1 |
| Diethylene Triamine Penta Acetic acid | — | 0.5 | — | — | — |
| Diethylene Triamine Penta Methylene Phosphonic acid | 0.3 | 0.1 | 0.3 | 0.3 | 0.3 |
| Soil Suspending Alkoxylated Polyalkylenimine Polymer[3] | 0.8 | 0.5 | — | — | 0.8 |
| Zwitterionic ethoxylated quaternized sulfated hexamethylene diamine[4] | 1 | 1 | 0.9 | 1 | 1 |
| Grease Cleaning Alkoxylated Polyalkylenimine Polymer[5] | 0.4 | 0.4 | — | 0.2 | — |
| PEG-PVAc Polymer[6] | — | 0.5 | — | — | — |
| Monoethanolamine Borate | 2.0 | 1.0 | 2.0 | 2.0 | 2.0 |
| 4 - Formyl Phenyl Boronic Acid | — | 0.03 | — | — | — |
| Sodium formate | 0.4 | 0.4 | 0.4 | 0.4 | 0.4 |
| Calcium chloride | 0.05 | 0.05 | 0.05 | 0.05 | 0.05 |
| dibenzyl (2S,2'S)-1,1'-(propane-1,3-diylbis(azanediyl))bis(3-methyl-1-oxobutane-2,1-diyl)dicarbamate | 0.2 | 0.24 | 0.2 | 0.28 | 0.28 |
| Acticide MBS 2550 | 0.005 | 0.005 | 0.005 | 0.005 | 0.005 |
| Perfume Microcapsules | — | — | — | 0.2 | — |
| Mica | — | — | — | — | 0.05 |
| Silicone suds suppressor | — | 0.1 | — | — | — |
| Water, perfumes, dyes, neutralizers, and other optional components (pH to 8.0-8.2) | to 100% | to 100% | to 100% | to 100% | to 100% |

[1] Available from Genencor International, South San Francisco, CA.
[2] Available from Novozymes, Denmark.
[3] 600 g/mol molecular weight polyethylenimine core with 20 ethoxylate groups per —NH. Available from BASF (Ludwigshafen, Germany)
[4] Described in WO 01/05874 and available from BASF (Ludwigshafen, Germany)
[5] 600 g/mol molecular weight polyethylenimine core with 24 ethoxylate groups per —NH and 16 propoxylate groups per —NH. Available from BASF (Ludwigshafen, Germany).
[6] PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).

Examples 5A to 5T

Hand-Dish Washing Fluid Detergent Compositions Comprising Amido-Gellants

Hand-dish washing liquid detergent compositions may be prepared by mixing together the ingredients listed in the proportions shown:

TABLE 9

Hand-dish washing fluid detergent compositions comprising amido-gellants:

| | Ex 5A | Ex 5B | Ex 5C | Ex 5D | Ex 5E | Ex 5F |
|---|---|---|---|---|---|---|
| Alkyl Ethoxy Sulfate AE0.6S | 22.0 | 19.0 | 27.0 | 20.0 | 22.0 | 22.0 |
| Linear C12-C14 Amine oxide | 6.0 | 4.5 | — | — | 6.0 | 5.0 |
| C9-C11 alkyl EO8 ethoxylate | 7.0 | — | — | — | — | — |
| L-Glutamic acid-N,N-di(acetic acid) tetrasodium salt | 1.0 | — | — | 0.1 | — | — |
| Sodium Citrate | — | 1.0 | — | 0.5 | 0.8 | — |
| Solvent: ethanol, isopropylalcohol, ... | 2.5 | 4.0 | 3.0 | 2.0 | 3.0 | 2.5 |
| Polypropylene glycol MW2000 | 1.0 | 0.5 | 1.0 | — | 2.0 | 1.0 |
| Sodium Chloride | 0.5 | 1.0 | 1.0 | 0.5 | 0.5 | 0.5 |

TABLE 9-continued

Hand-dish washing fluid detergent compositions comprising amido-gellants:

| | Ex 5A | Ex 5B | Ex 5C | Ex 5D | Ex 5E | Ex 5F |
|---|---|---|---|---|---|---|
| dibenzyl (2S,2'S)-1,1'-(propane-1,3-diylbis(azanediyl))bis(3-methyl-1-oxobutane-2,1-diyl)dicarbamate | 0.50 | 0.20 | 0.30 | 0.15 | 0.25 | 0.20 |

Minors and Balance with water up to 100%

TABLE 10

Hand-dish washing fluid detergent compositions comprising amido-gellants:

| | Ex 5G | Ex 5H | Ex 5I | Ex 5J |
|---|---|---|---|---|
| Alkyl Ethoxy Sulfate AE1.0S | 13 | 16 | 17 | 20 |
| C12-C14 Amine oxide | 4.5 | 5.5 | 4.0 | 4.5 |
| C9-C11 alkyl EO8 ethoxylate | 4 | 4 | — | — |
| L-Glutamic acid-N,N-di(acetic acid) tetrasodium salt | 0.7 | — | — | — |
| Sodium Citrate | — | — | 0.2 | — |
| Solvent: ethanol, isopropylalcohol, . . . | 2.0 | 2.0 | 2.0 | 1.5 |
| Polypropylene glycol MW 2000 | 0.5 | 0.3 | 0.5 | 0.8 |
| Sodium Chloride | 0.5 | 0.8 | 0.4 | 0.5 |
| dibenzyl (2S,2'S)-1,1'-(hexane-1,6-diylbis(azanediyl))bis(1-oxo-3-phenylpropane-2,1-diyl)dicarbamate | 0.15 | 0.12 | 0.18 | 0.21 |

Minors and Balance with water up to 100%

TABLE 11

Hand-dish washing fluid detergent compositions comprising amido-gellants:

| | Ex 5K | Ex 5L | Ex 5M | Ex 5N | Ex 5O |
|---|---|---|---|---|---|
| Linear Alkylbenzene Sulfonate | 21.0 | 21.0 | 12.0 | 13.0 | — |
| Alkyl Ethoxy Sulfate AE1.0S | — | — | 14.0 | 5.0 | 17.0 |
| C12-14 alpha olefin sulfonate | — | — | — | — | 6.0 |
| Coco amido propyl Amine Oxide | — | — | — | 1.0 | 5.0 |
| alkylpolyglucoside | — | 2.0 | — | — | — |
| C9-C11 alkyl EO8 ethoxylate | 5.0 | 4.0 | 8.0 | 4.0 | 3.0 |
| L-Glutamic acid-N,N-di(acetic acid) tetrasodium salt | 0.5 | — | — | — | — |
| dibenzyl (2S,2'S)-1,1'-(propane-1,3-diylbis(azanediyl))bis(1-oxo-3-phenylpropane-2,1-diyl)dicarbamate | 0.30 | 0.10 | 0.10 | 0.20 | 0.15 |

Minors and Balance with water up to 100%

TABLE 12

Hand-dish washing fluid detergent compositions comprising amido-gellants:

| | Ex 5P | Ex 5Q | Ex 5R | Ex 5S | Ex 5T |
|---|---|---|---|---|---|
| Alkyl Ethoxy Sulfate AE2.0S | 17.0 | 12.0 | 24.0 | 18.0 | 29.0 |
| C12-14 alpha olefin sulfonate | — | — | 1.0 | — | — |
| Paraffin Sulfonate (C15) | 9.0 | 1.0 | 1.0 | — | — |
| Coco amido propyl amine oxide | — | 6.0 | — | — | 1.0 |
| Coco amido propyl Betaine | — | — | — | 5.0 | — |
| C12-C14 Akylpolyglucoside | — | 3.0 | 2.0 | — | — |
| C9-C11 alkyl EO8 ethoxylate | 8.0 | 2.0 | — | — | — |

TABLE 12-continued

Hand-dish washing fluid detergent compositions comprising amido-gellants:

| | Ex 5P | Ex 5Q | Ex 5R | Ex 5S | Ex 5T |
|---|---|---|---|---|---|
| L-Glutamic acid-N,N-di(acetic acid) tetrasodium salt | 0.5 | — | 0.5 | — | — |
| Polypropylene glycol MW2000 | 1.0 | 1.0 | — | 0.5 | 0.5 |
| N,N'-(2S,2'S)-1,1'-(octane-1,8-diylbis(azanediyl))bis(3-methyl-1-oxobutane-2,1-diyl)dibenzamide | 0.10 | 0.15 | 0.10 | 0.20 | 0.15 |

Minors and Balance with water up to 100%

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

"While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention."

What is claimed is:
1. A fluid detergent composition comprising:
   a. from 1% to 70% by weight of a surfactant selected from the group: anionic, nonionic surfactants and mixtures thereof;
   b. from 0.01 wt % to 10 wt % of a di-amido gellant, wherein the di-amido gellant has the following formula:

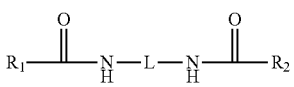

[I]

wherein:
R$_1$ and R$_2$ may be the same or different and both have the structure:

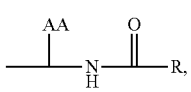

wherein:

AA is selected from the group consisting of:

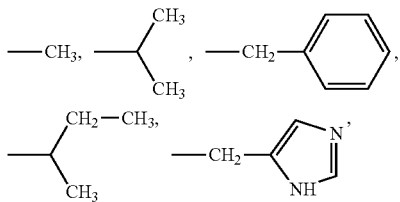

and R is selected from the group:

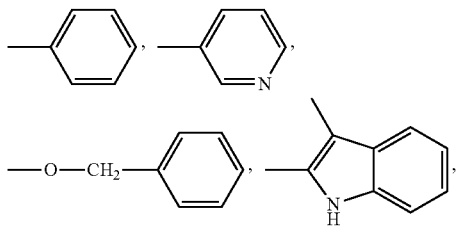

and

L is an aliphatic linking group with a backbone chain of from 2 to 20 carbon atoms, having a molecular weight from 14 to 500 g/mol.

2. The fluid detergent composition according to claim 1, wherein the di-amido gellant has a molecular weight from 150 to 1500 g/mol.

3. The fluid detergent composition according to claim 1, wherein the di-amido gellant has a minimum gelling concentration (MGC) of from 0.1 to 100 mg/mL.

4. The fluid detergent composition according to claim 1, wherein the di-amido gellant is selected from the group consisting of: dibenzyl (2S,2'S)-1,1'-(ethane-1,2-diylbis(azanediyl))bis(3-methyl-1-oxobutane-2,1-diyl)dicarbamate; dibenzyl (2S,2'S)-1,1'-(propane-1,3-diylbis(azanediyl))bis(3-methyl-1-oxobutane-2,1-diyl)dicarbamate; dibenzyl (2S,2'S)-1,1'-(butane-1,4-diylbis(azanediyl))bis(3-methyl-1-oxobutane-2,1-diyl)dicarbamate; dibenzyl (2S,2'S)-1,1'-(pentane-1,5-diylbis(azanediyl))bis(3-methyl-1-oxobutane-2,1-diyl)dicarbamate; dibenzyl (2S,2'S)-1,1'-(hexane-1,6-diylbis(azanediyl))bis(3-methyl-1-oxobutane-2,1-diyl)dicarbamate; dibenzyl (2S,2'S)-1,1'-(heptane-1,7-diylbis(azanediyl))bis(3-methyl-1-oxobutane-2,1-diyl)dicarbamate; dibenzyl (2S,2'S)-1,1'-(octane-1,8-diylbis(azanediyl))bis(3-methyl-1-oxobutane-2,1-diyl)dicarbamate; dibenzyl (2S,2'S)-1,1'-(nonane-1,9-diylbis(azanediyl))bis(3-methyl-1-oxobutane-2,1-diyl)dicarbamate; dibenzyl (2S,2'S)-1,1'-(decane-1,10-diylbis(azanediyl))bis(3-methyl-1-oxobutane-2,1-diyl)dicarbamate; dibenzyl (2S,2'S)-1,1'-(undecane-1,11-diylbis(azanediyl))bis(3-methyl-1-oxobutane-2,1-diyl)dicarbamate; dibenzyl (2S,2'S)-1,1'-(dodecane-1,12-diylbis(azanediyl))bis(3-methyl-1-oxobutane-2,1-diyl)dicarbamate; dibenzyl (2S,2'S)-1,1'-(tridecane-1,13-diylbis(azanediyl))bis(3-methyl-1-oxobutane-2,1-diyl)dicarbamate; dibenzyl (2S,2'S)-1,1'-(hexadecane-1,16-diylbis(azanediyl))bis(3-methyl-1-oxobutane-2,1-diyl)dicarbamate; dibenzyl (2S,2'S)-1,1'-(octodecane-1,18-diylbis(azanediyl))bis(3-methyl-1-oxobutane-2,1-diyl)dicarbamate; dibenzyl (2S,2'S)-1,1'-(tetradecane-1,14-diylbis(azanediyl))bis(3-methyl-1-oxobutane-2,1-diyl)dicarbamate; N,N'-(2S,2'S)-1,1'-(ethane-1,2-diylbis(azanediyl))bis(3-methyl-1-oxobutane-2,1-diyl)dibenzamide; N,N'-(2S,2'S)-1,1'-(propane-1,3-diylbis(azanediyl))bis(3-methyl-1-oxobutane-2,1-diyl)dibenzamide; N,N'-(2S,2'S)-1,1'-(butane-1,4-diylbis(azanediyl))bis(3-methyl-1-oxobutane-2,1-diyl)dibenzamide; N,N'-(2S,2'S)-1,1'-(pentane-1,5-diylbis(azanediyl))bis(3-methyl-1-oxobutane-2,1-diyl)dibenzamide; N,N'-(2S,2'S)-1,1'-(hexane-1,6-diylbis(azanediyl))bis(3-methyl-1-oxobutane-2,1-diyl)dibenzamide; N,N'-(2S,2'S)-1,1'-(heptane-1,7-diylbis(azanediyl))bis(3-methyl-1-oxobutane-2,1-diyl)dibenzamide; N,N'-(2S,2'S)-1,1'-(octane-1,8-diylbis(azanediyl))bis(3-methyl-1-oxobutane-2,1-diyl)dibenzamide; N,N'-(2S,2'S)-1,1'-(nonane-1,9-diylbis(azanediyl))bis(3-methyl-1-oxobutane-2,1-diyl)dibenzamide; N,N'-(2S,2'S)-1,1'-(decane-1,10-diylbis(azanediyl))bis(3-methyl-1-oxobutane-2,1-diyl)dibenzamide; N,N'-(2S,2'S)-1,1'-(undecane-1,11-diylbis(azanediyl))bis(3-methyl-1-oxobutane-2,1-diyl)dibenzamide; N,N'-(2S,2'S)-1,1'-(dodecane-1,12-diylbis(azanediyl))bis(3-methyl-1-oxobutane-2,1-diyl)dibenzamide; N,N'-(2S,2'S)-1,1'-(tridecane-1,13-diylbis(azanediyl))bis(3-methyl-1-oxobutane-2,1-diyl)dibenzamide; N,N'-(2S,2'S)-1,1'-(hexadecane-1,16-diylbis(azanediyl))bis(3-methyl-1-oxobutane-2,1-diyl)dibenzamide; N,N'-(2S,2'S)-1,1'-(octadecane-1,18-diylbis(azanediyl))bis(3-methyl-1-oxobutane-2,1-diyl)dibenzamide, N,N'-(2S,2'S)-1,1'-(tetradecane-1,14-diylbis(azanediyl))bis(3-methyl-1-oxobutane-2,1-diyl)dibenzamide; dibenzyl(2S,2'S)-1,1'-(ethane-1,2-diylbis(azanediyl))bis(1-oxopropane-2,1-diyl)dicarbamate; dibenzyl(2S,2'S)-1,1'-(propane-1,3-diylbis(azanediyl))bis(1-oxopropane-2,1-diyl)dicarbamate; dibenzyl(2S,2'S)-1,1'-(butane-1,4-diylbis (azanediyl))bis(1-oxopropane-2,1-diyl)dicarbamate; dibenzyl(2S,2'S)-1,1'-(pentane-1,5-diylbis(azanediyl))bis(1-oxopropane-2,1-diyl)dicarbamate; dibenzyl(2S,2'S)-1,1'-(hexane-1,6-diylbis (azanediyl))bis(1-oxopropane-2,1-diyl)dicarbamate; dibenzyl(2S,2'S)-1,1'-(heptane-1,7-diylbis(azanediyl))bis(1-oxopropane-2,1-diyl)dicarbamate; dibenzyl(2S,2'S)-1,1'-(octane-1,8-diylbis(azanediyl))bis(1-oxopropane-2,1-diyl)dicarbamate; dibenzyl(2S,2'S)-1,1'-(nonane-1,9-diylbis (azanediyl))bis(1-oxopropane-2,1-diyl)dicarbamate; dibenzyl(2S,2'S)-1,1'-(decane-1,10-diylbis (azanediyl))bis(1-oxopropane-2,1-diyl)dicarbamate; dibenzyl(2S,2'S)-1,1'-(undecane-1,11-diylbis (azanediyl))bis(1-oxopropane-2,1-diyl)dicarbamate; dibenzyl(2S,2'S)-1,1'-(dodecane-1,12-diylbis(azanediyl))bis(1-oxopropane-2,1-diyl)dicarbamate; dibenzyl(2S,2'S)-1,1'-(tridecane-1,13-diylbis(azanediyl))bis(1-oxopropane-2,1-diyl)dicarbamate; dibenzyl(2S,2'S)-1,1'-(hexadecane-1,16-diylbis(azanediyl))bis(1-oxopropane-2,1-diyl)dicarbamate; dibenzyl (2S,2'S)-1,1'-(octadecane-1,18-diylbis(azanediyl))bis(1-oxopropane-2,1-diyl)dicarbamate; dibenzyl(2S,2'S)-1,1'-(tetradecane-1,14-diylbis(azanediyl))bis(1-oxopropane-2,1-diyl)dicarbamate; dibenzyl(2S,2'S)-1,1'-(ethane-1,2-diylbis(azanediyl))bis(1-oxo-3-phenylpropane-2,1-diyl)dicarbamate; dibenzyl(2S,2'S)-1,1'-(propane-1,3-diylbis(azanediyl))bis(1-oxo-3-phenylpropane-2,1-diyl)dicarbamate; dibenzyl(2S,2'S)-1,1'-(butane-1,4-diylbis(azanediyl))bis(1-oxo-3-phenylpropane-2,1-diyl)dicarbamate; dibenzyl (2S,2'S)-1,1'-(pentane-1,5-diylbis(azanediyl))bis(1-oxo-3-phenylpropane-2,1-diyl)dicarbamate; dibenzyl(2S,2'S)-1,1'-(hexane-1,6-diylbis(azanediyl))bis(1-oxo-3-phenylpropane-2,1-diyl)dicarbamate; dibenzyl(2S,2'S)-1,1'-(heptane-1,7-diylbis(azanediyl))bis(1-oxo-3-phenylpropane-2,1-diyl)dicarbamate; dibenzyl(2S,2'S)-1,1'-(nonane-1,9-diylbis(azanediyl))bis(1-oxo-3-phenylpropane-2,1-diyl)dicarbamate,dibenzyl(2S,2'S)-1,1'-(decane-1,10-diylbis (azanediyl))

bis(1-oxo-3-phenylpropane-2,1-diyl)dicarbamate; dibenzyl (2S,2'S)-1,1'-(undecane-1,11-diylbis(azanediyl))bis(1-oxo-3-phenylpropane-2,1-diyl)dicarbamate; dibenzyl (2S,2'S)-1,1'-(dodecane-1,12-diylbis(azanediyl))bis(1-oxo-3-phenyl-propane-2,1-diyl)dicarbamate; dibenzyl(2S,2'S)-1,1'-(tridecane-1,13-diylbis(azanediyl))bis(1-oxo-3-phenylpropane-2,1-diyl)dicarbamate; dibenzyl(2S,2'S)-1,1'-(hexadecane-1,16-diylbis(azanediyl))bis(1-oxo-3-phenylpropane-2,1-diyl)dicarbamate; dibenzyl (2S,2'S)-1,1'-(octadecane-1,18-diylbis(azanediyl))bis(1-oxo-3-phenylpropane-2,1-diyl)dicarbamate; dibenzyl(2S,2'S)-1,1'-(tetradecane-1,14-diylbis(azanediyl))bis(1-oxo-3-phenylpropane-2,1-diyl)dicarbamate; N,N'-(2S,2'S)-1,1'-(nonane-1,9-diylbis (azanediyl))bis(1-oxo-3-phenylpropane-2,1-diyl)dibenzamide; N,N'-(2S,2'S)-1,1'-(decane-1,10-diylbis(azanediyl))bis(1-oxo-3-phenylpropane-2,1-diyl)dibenzamide,; N,N'-(2S,2'S)-1,1'-(undecane-1,11-diylbis(azanediyl))bis(1-oxo-3-phenylpropane-2,1-diyl)dibenzamide; N,N'-(2S,2'S)-1,1'-(dodecane-1,12-diylbis(azanediyl))bis(1-oxo-3-phenylpropane-2,1-diyl)dibenzamide; N,N'-(2S,2'S)-1,1'-(tridecane-1,13-diylbis(azanediyl))bis(1-oxo-3-phenylpropane-2,1-diyl)dibenzamide; N,N'-(2S,2'S)-1,1'-(hexadecane-1,16-diylbis(azanediyl))bis(1-oxo-3-phenylpropane-2,1-diyl)dibenzamide,; N,N'-(2S,2'S)-1,1'-(octadecane-1,18-diylbis(azanediyl))bis(1-oxo-3-phenylpropane-2,1-diyl)dibenzamide; N,N'-(2S,2'S)- 1,1'-(tetradecane-1,14-diylbis(azanediyl))bis(1-oxo-3-phenylpropane-2,1-diyl)dibenzamide; N,N'-(2S,2'S)-1,1'-(ethane-1,2-diylbis(azanediyl))bis(1-oxo-3-phenylpropane-2,1-diyl)dibenzamide; N,N'-(2S,2'S)-1,1'-(propane-1,3-diylbis(azanediyl))bis(1-oxo-3-phenylpropane-2,1-diyl) dibenzamide; N,N'-(2S,2'S)-1,1'-(butane-1,4-diylbis (azanediyl))bis(1-oxo-3-phenylpropane-2,1-diyl) dibenzamide; N,N'-(2S,2'S)-1,1'-(pentane-1,5-diylbis (azanediyl))bis(1-oxo-3-phenylpropane-2,1-diyl) dibenzamide; N,N'-(2S,2'S)-1,1'-(hexane-1,6-diylbis (azanediyl))bis(1-oxo-3-phenylpropane-2,1-diyl) dibenzamide; N,N'-(2S,2'S)-1,1'-(heptane-1,7-diylbis (azanediyl))bis(1-oxo-3-phenylpropane-2,1-diyl) dibenzamide; N,N'-(2S,2'S)-1,1'-(octane-1,8-diylbis (azanediyl))bis(1-oxo-3-phenylpropane-2,1-diyl) dibenzamide; N,N'-(2S,2'S)- 1,1'-(ethane-1,2-diylbis (azanediyl))bis(1-oxopropane-2,1-diyl)dibenzamide; N,N'-(2S,2'S)-1,1'-(propane-1,3-diylbis(azanediyl))bis(1-oxopropane-2,1-diyl)dibenzamide; N,N'-(2S,2'S)-1,1'-(butane-1,4-diylbis(azanediyl))bis(1-oxopropane-2,1-diyl) dibenzamide; N,N'-(2S,2'S)-1,1'-(pentane-1,5-diylbis (azanediyl))bis(1-oxopropane-2,1-diyl)dibenzamide; N,N'-(2S,2'S)-1,1'-(hexane-1,6-diylbis(azanediyl))bis(1-oxopropane-2,1-diyl)dibenzamide; N,N'-(2S,2'S)-1,1'-(heptane-1,7-diylbis(azanediyl))bis(1-oxopropane-2,1-diyl) dibenzamide; N,N'-(2S,2'S)-1,1'-(octane-1,8-diylbis (azanediyl))bis(1-oxopropane-2,1-diyl)dibenzamide; N,N'-(2S,2'S)-1,1'-(nonane-1,9-diylbis(azanediyl))bis(1-oxopropane-2,1-diyl)dibenzamide; N,N'-(2S,2'S)-1,1'-(decane-1,10-diylbis(azanediyl))bis(1-oxopropane-2,1-diyl) dibenzamide; N,N'-(2S,2'S)-1,1'-(undecane-1,11-diylbis (azanediyl))bis(1-oxopropane-2,1-diyl)dibenzamide, N,N'-(2S,2'S)-1,1'-(dodecane-1,12-diylbis(azanediyl))bis(1-oxopropane-2,1-diyl)dibenzamide; N,N'-(2S,2'S)-1,1'-(tridecane-1,13-diylbis(azanediyl))bis(1-oxopropane-2,1-diyl)dibenzamide; N,N'-(2S,2'S)-1,1'-(hexadecane-1,16-diylbis(azanediyl))bis(1-oxopropane-2,1-diyl)dibenzamide; N,N'-(2S,2'S)-1,1'-(octadecane-1,18-diylbis(azanediyl))bis (1-oxopropane-2,1-diyl)dibenzamide; N,N'-(2S,2'S)-1,1'-(tetradecane-1,14-diylbis(azanediyl))bis(1-oxopropane-2,1-diyl)dibenzamide; dibenzyl(2S,2'S)-1,1'-(octane-1,8-diylbis (azanediyl))bis(1-oxo-3-phenylpropane-2,1-diyl) dicarbamate; and mixtures of thereof.

5. The fluid detergent composition according to claim 1, wherein the composition comprises:
   a. from 0.0001% to 8% by weight of a detersive enzyme, and
   wherein said composition has a neat pH from 6.5 to 10.5.

6. The fluid detergent composition according to claim 5, wherein the detersive enzyme is selected from the group consisting of: proteases, amylases, cellulases, lipases, xylogucanases, pectate lyases, mannanases, bleaching enzymes, cutinases, and mixtures thereof.

7. The fluid detergent composition according to claim 1, wherein the composition is a fluid laundry detergent composition comprising:
   a. from 0.1% to 12% by weight of the bleach or bleach system, and
   wherein said composition has a neat pH of from 6.5 to 10.5.

8. The fluid detergent composition according to claim 1, wherein the composition is a fluid laundry bleach additive comprising:
   a. from 0.1% to 12% by weight of a bleach or bleach system, and
   wherein said composition has a neat pH of from 2 to 6.

9. The fluid detergent composition according to claim 1, wherein the surfactant is an anionic surfactant selected from the group consisting of: C11-C18 alkyl benzene sulfonates, C10-C20 branched-chain and random alkyl sulfates, C10-C18 alkyl ethoxy sulfates wherein x is from 1-30, mid-chain branched alkyl sulfates, mid-chain branched alkyl alkoxy sulfates, C10-C18alkyl alkoxy carboxylates comprising 1-5 ethoxy units, modified alkylbenzene sulfonate, C12-C20 methyl ester sulfonate, C10-C18 alpha-olefin sulfonate, C6-C20 sulfosuccinates, and mixtures thereof.

10. The fluid detergent composition according to claim 1, wherein the composition further comprises an adjunct ingredient selected from the group consisting of: cationic surfactants, amphoteric surfactants, zwitterionic surfactants, non-aminofunctional organic solvents, enzymes, enzyme stabilizers, amphiphilic alkoxylated grease cleaning polymers, clay soil cleaning polymers, soil release polymers, soil suspending polymers, bleaching systems, optical brighteners, hueing dyes, particulate material, perfume and other odour control agents, hydrotropes, suds suppressors, fabric care benefit agents, pH adjusting agents, dye transfer inhibiting agents, preservatives, non-fabric substantive dyes and mixtures thereof.

11. The fluid detergent composition according to claim 1, wherein said fluid detergent composition is enclosed within a water soluble pouch material.

* * * * *